(12) United States Patent
Wendorf et al.

(10) Patent No.: US 9,393,215 B2
(45) Date of Patent: Jul. 19, 2016

(54) NANOPARTICLES FOR USE IN IMMUNOGENIC COMPOSITIONS

(75) Inventors: Janet R. Wendorf, Redwood City, CA (US); Manmohan Singh, Lexington, MA (US); Derek T. O'Hagan, Winchester, MA (US)

(73) Assignee: Novartis AG, Basel (CH)

( * ) Notice: Subject to any disclaimer, the term of this patent is extended or adjusted under 35 U.S.C. 154(b) by 1574 days.

(21) Appl. No.: 12/095,655

(22) PCT Filed: Dec. 1, 2006

(86) PCT No.: PCT/US2006/046212
§ 371 (c)(1),
(2), (4) Date: Jul. 8, 2010

(87) PCT Pub. No.: WO2008/051245
PCT Pub. Date: May 2, 2008

(65) Prior Publication Data
US 2010/0285135 A1   Nov. 11, 2010

Related U.S. Application Data

(60) Provisional application No. 60/741,860, filed on Dec. 2, 2005, provisional application No. 60/775,265, filed on Feb. 21, 2006.

(51) Int. Cl.
| | |
|---|---|
| A61K 9/14 | (2006.01) |
| A61K 39/00 | (2006.01) |
| A61K 39/002 | (2006.01) |
| A61K 39/09 | (2006.01) |
| A61K 39/095 | (2006.01) |
| A61K 39/10 | (2006.01) |
| A61K 39/12 | (2006.01) |
| A61K 39/13 | (2006.01) |
| A61K 39/145 | (2006.01) |
| A61K 39/165 | (2006.01) |
| A61K 39/20 | (2006.01) |
| A61K 39/21 | (2006.01) |
| A61K 39/25 | (2006.01) |
| A61K 39/29 | (2006.01) |
| A61K 39/385 | (2006.01) |
| A61K 31/04 | (2006.01) |
| A61K 31/10 | (2006.01) |
| A61K 31/12 | (2006.01) |
| A61K 33/00 | (2006.01) |
| A61K 35/00 | (2006.01) |
| A61K 9/51 | (2006.01) |
| A61K 39/39 | (2006.01) |

(52) U.S. Cl.
CPC .............. *A61K 9/5153* (2013.01); *A61K 39/39* (2013.01); *A61K 2039/55555* (2013.01)

(58) Field of Classification Search
None
See application file for complete search history.

(56) References Cited

U.S. PATENT DOCUMENTS

| | | | |
|---|---|---|---|
| 5,049,322 A * | 9/1991 | Devissaguet et al. | 264/4.1 |
| 5,118,528 A | 6/1992 | Fessi et al. | |
| 5,133,908 A | 7/1992 | Stainmesse et al. | |
| 5,302,401 A * | 4/1994 | Liversidge et al. | 424/501 |
| 5,565,188 A * | 10/1996 | Wong et al. | 424/489 |
| 6,139,870 A | 10/2000 | Verrecchia | |
| 6,221,575 B1 * | 4/2001 | Roser et al. | 435/2 |
| 6,884,435 B1 * | 4/2005 | O'Hagan | A61K 9/1647 424/455 |
| 7,906,620 B2 * | 3/2011 | Eisenbach et al. | 530/350 |
| 2002/0136776 A1 | 9/2002 | Fang et al. | |
| 2005/0139144 A1 | 6/2005 | Muller | |
| 2005/0244505 A1 * | 11/2005 | Higbee et al. | 424/489 |

FOREIGN PATENT DOCUMENTS

| | | |
|---|---|---|
| WO | 96/20698 | 7/1996 |
| WO | 9702810 A3 | 1/1997 |
| WO | 9814174 A1 | 4/1998 |
| WO | 9945966 A1 | 9/1999 |
| WO | 00/06123 A1 | 2/2000 |
| WO | 0006123 A1 | 2/2000 |
| WO | 0226209 A2 | 4/2002 |
| WO | 03092623 A2 | 11/2003 |
| WO | 2004032980 A1 | 4/2004 |
| WO | 2008/051245 A2 | 5/2008 |

OTHER PUBLICATIONS

Birnbaum, et al. (2000) J. Nanoparticle Research: 2: 173-181.*
Pluschke, et al. (1985) Infection and Immunity, 49(2): 365-70.*
A. Pashine et al., Targeting the innate immune response with improved vaccine adjuvants, Nature Medicine Supplement. 11(4), Apr. 2005, pp. S63-S68.
K.S. Rosenthal et al., Vaccine: All Things Considered, Clinical and Vaccine Immunology, Aug. 2006, pp. 821-829.
J. Wendorf et al., A practical Approach to the use of Nanoparticles for Vaccine Delivery, Journal of Pharmaceutical Sciences 95(12), 2006, 12 pp.
U. Bilati et al., Development of a nanoprecipitation method intended for the entrapment of hydrophillic drugs into nanoparticles, European Journal of Pharmaceutical Sciences, 24 (2005), pp. 67-75.
D.T. Birnbaum et al., Optimization of preparation techniques for poly(lactic-acid-co-glycolic acid) nanoparticles, Journal of Nanoparticle Research 2 (2000), pp. 173-181.

(Continued)

*Primary Examiner* — Robert M Kelly
(74) *Attorney, Agent, or Firm* — Helen Lee; Virginia Campen

(57) ABSTRACT

Disclosed herein are sterile-filtered lyophilized nanoparticle compositions which contain at least one biodegradable polymer, at least one surfactant, at least one cryoprotective agent and at least one antigen. Also disclosed are methods of making and using such compositions and kits supplying such compositions.

49 Claims, 1 Drawing Sheet

(56) References Cited

OTHER PUBLICATIONS

H. Fessi et al., Nanocapsule formation by interfacial polymer deposition following solvent displacement, International Journal of Pharmaceutics 55(1), 1989, pp. R1-R4.

Leena Peltonen et al., "The Effect of Cosolvents on the Formulation of Nanoparticles From Low-Molecular-Weight Poly(l)lactide," AAPS PharmSciTech, 2002, 3 (4): 1-7.

Tobias Jung et al., "Loading of Tetanus Toxoid to Biodegradable Nanoparticles from Branched Poly(Sulfobutyl-Polyvinyl Alcohol)-g-(Lactide-Co-Glycolide) Nanoparticles by Protein Adsorption: A Mechanistic Study," Pharmaceutical Research, Aug. 2002, 19 (8): 1105-1113.

Christine Oster, "Microparticular and Nanoparticular DNA Delivery Systems as Adjuvants for DNA Immunization," dissertation, University of Marburg, Germany, 2004.

Manmohan Singh, "Anionic Microparticles are a Potent Delivery System for Recombinant Antigens from Neisseria meningitidis Serotype B," Journal of Pharmaceutical Sciences, Feb. 2004, vol. 93: 273-282.

S.Y. Kim et al., "Oral Immunization with Helicobactrer pylori-Loaded Poly(D,L-Lactide-Co-Glycolide) Nanoparticles", Helicabacter, vol. 4., No. 1, pp. 33-39. XP002977235, Year: 1999.

A. Cui et al., "Physical Characterization and Acrophage Cell Uptake of Mannan-Coated Nanoparticles", Drug Development and Industrial Pharmacy, vol. 29, No. 6, 2003, pp. 689-700. XP008090137.

J. Samuel et al., "Polmeric Nanoparticles for Targeted Delivery of Therapeutic Vaccines to Dendritic Cells," Proceedings of the International Conference on MEMS, Nano and Smart Systems, 2003, XP 010650296.

M. Auvillain et al., "Lyophilisation de vecteurs colloidaux sumbicroniques", S.T.P. Pharma, vol. 5, No. 11, 1989, pp. 738-744. XP008090138.

\* cited by examiner

NANOPARTICLES FOR USE IN IMMUNOGENIC COMPOSITIONS

STATEMENT OF RELATED APPLICATIONS

This application claims the benefit of U.S. Provisional Patent Application Ser. No. 60/741,860, filed Dec. 2, 2005, entitled "Nanoparticles For Use In Immunogenic Compositions." This application also claims the benefit of U.S. Provisional Patent Application Ser. No. 60/775,265, filed Feb. 21, 2006, entitled "Nanoparticles For Use In Immunogenic Compositions." Both of the prior applications are incorporated by reference herein in their entireties.

BACKGROUND

Particulate carriers have been used with adsorbed or entrapped antigens in attempts to elicit adequate immune responses. Such carriers present multiple copies of a selected antigen to the immune system and are believed to promote trapping and retention of antigens in local lymph nodes. The particles can be phagocytosed by macrophages and can enhance antigen presentation through cytokine release.

For example, commonly owned International Publication No. WO 98/33487 and co-pending U.S. Patent Application Publication No. 2003/0049298 describe the use of antigen-adsorbed and antigen-encapsulated microparticles to stimulate immunological responses, including cell-mediated immunological responses, as well as methods of making the microparticles. Polymers used to form the microparticles include poly(lactide) and poly(lactide-co-glycolide) (PLG).

Commonly owned International Publication No. WO 00/06123 and WO 01/36599 and U.S. Pat. No. 6,884,435 disclose methods of making microparticles having adsorbed macromolecules, including polynucleotides and polypeptide antigens. The microparticles comprise, for example, a polymer such as a poly(alpha-hydroxy acid) (e.g., PLG, a polyhydroxy butyric acid, a polycaprolactone, a polyorthoester, a polyanhydride, and the like) and are formed using, for example, cationic, anionic or nonionic detergents. Microparticles containing anionic detergents, such as PLG microparticles containing sodium dodecyl sulfate (SDS), can be used with positively charged macromolecules, such as polypeptides. Microparticles containing cationic detergents, such as PLG microparticles with CTAB (also known as cetrimide or cetyl trimethyl ammonium bromide), can be used with negatively charged macromolecules, such as DNA. The use of such microparticles to stimulate immunological responses, including cell-mediated immunological responses, is also disclosed.

SUMMARY OF THE INVENTION

In one aspect, the present invention provides sterile lyophilized nanoparticle compositions which comprise the following: at least one biodegradable polymer, at least one surfactant, at least one cryoprotective agent and at least one antigen.

In some embodiments, lyophilized particles have a Z average or D(v,0.5) value that is less than 250 nm, for example ranging from 250 nm to 200 nm to 150 nm to 100 nm or less.

Such compositions are useful, for example, in that they are immunogenic and in that they readily form nanoparticle suspensions. For instance, upon mixing lyophilized nanoparticle compositions of the present invention with distilled water in a concentration of 0.005 g/ml (range of 5-10 mg/mL), an immunogenic nanoparticle suspension can be spontaneously formed in which the Z average or D(v,0.5) value of said suspended nanoparticles is less than 250 nm, for example ranging from 250 nm to 200 nm to 150 nm to 100 nm or less.

In certain embodiments, the biodegradable polymers are synthetic biodegradable polymers, for example, selected from poly($\alpha$-hydroxy acids), polyhydroxy butyric acids, polycaprolactones, polyorthoesters, polyanhydrides, polycyanoacrylates, and combinations thereof, among others.

Examples of cryoprotective agents include polyols, carbohydrates and combinations thereof, among others.

Examples of surfactants include non-ionic surfactants, cationic surfactants and anionic surfactants, among others.

Antigens can be, for example, adsorbed on the surface of the nanoparticles, entrapped within the nanoparticles or both. Examples of antigens include polypeptide-containing antigens, polysaccharide-containing antigens, and polynucleotide-containing antigens, among others. Antigens can be derived, for example, from tumor cells and from pathogenic organisms such as viruses, bacteria, fungi and parasites.

In certain embodiments, the compositions of the present invention can comprise supplemental components, such as immunological adjuvants, which can be, for example, adsorbed to the surface of the nanoparticles, entrapped within the nanoparticles, or both. Examples of supplemental immunological adjuvants include CpG oligonucleotides, double-stranded RNA, *E. coli* heat-labile toxins, alum, liposaccharide phosphate compounds, and liposaccharide phosphate mimetics, among others.

Where two antigens, two immunological adjuvants, or one antigen and one immunological adjuvant are employed, they can be, for example, (a) adsorbed to the same population of nanoparticles, (b) each adsorbed to separate populations of nanoparticles, (c) one adsorbed to nanoparticles and the other in solution, (d) one adsorbed to nanoparticles and the other entrapped within the same population of nanoparticles, (e) one adsorbed to a first population of nanoparticles and the other entrapped within the a second population of nanoparticles, and so forth.

In other aspects, the present invention provides methods of producing nanoparticle compositions such as the foregoing.

In still other aspects, the present invention provides methods of delivering the nanoparticle compositions to a host animal (e.g., for therapeutic, prophylactic, or diagnostic purposes). The host animal is preferably a vertebrate animal, more preferably a mammal, and even more preferably a human. Delivery of the nanoparticle compositions of the invention can be performed by any known method.

In further aspects, the present invention provides kits comprising the nanoparticle compositions of the invention.

Compared to microparticle based technologies, such as those described above in the background of the invention, advantages of the present invention include ease of preparation (e.g., high-shear homogenization is not necessary and because the nanoparticles may be sterile filtered, the nanoparticle preparation process need not be strictly aseptic), and the ability to adsorb higher levels of antigens and other species to the surface of the nanoparticles, among other advantages.

These and other aspects, embodiments, and advantages of the present invention will become more readily apparent to those of ordinary skill in the art in view of the disclosure herein.

DETAILED DESCRIPTION OF THE INVENTION

Figure 1:
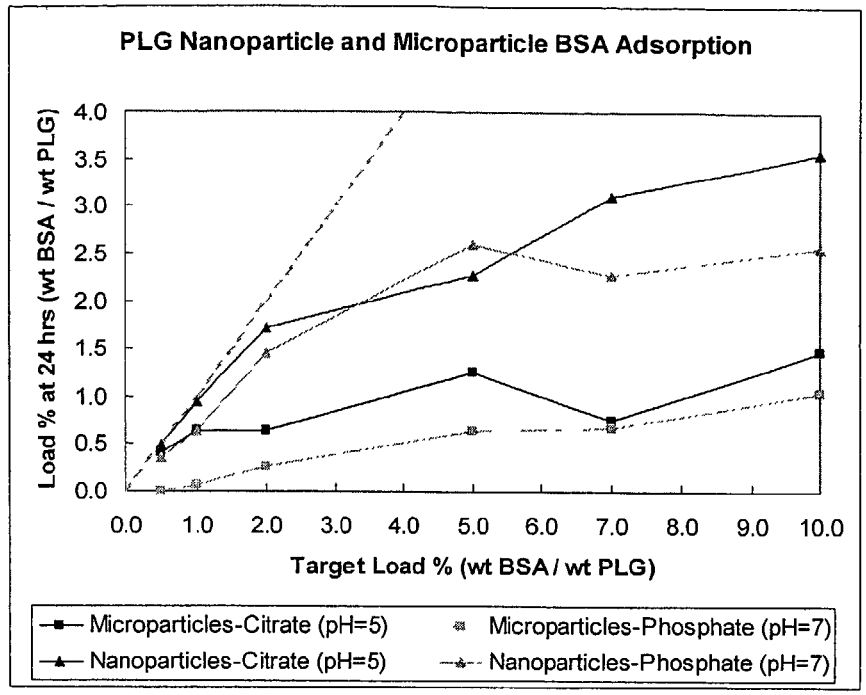
FIG. 1 depicts plots of BSA loading on PLG microparticles and nanoparticles at pH=5 and at pH=7.

The practice of the present invention will employ, unless otherwise indicated, conventional methods of chemistry, polymer chemistry, biochemistry, molecular biology, immunology and pharmacology, within the skill of the art. Such techniques are explained fully in the literature. See, e.g., *Remington's Pharmaceutical Sciences,* 18th ed. (Easton, Pa.: Mack Publishing Company, 1990); *Methods In Enzymology* (S. Colowick and N. Kaplan, eds., Academic Press, Inc.); Weir, D. M., *Handbook of Experimental Immunology,* Vols. I-IV, 5th ed. (Blackwell Publishers, 1996); Sambrook, J. et al., *Molecular Cloning: A Laboratory Manual,* 3rd ed. (Cold Spring Harbor Laboratory Press, 2001); Ausubel, F. M. et al., *Short Protocols In Molecular Biology,* 5th ed. (Current Protocols, 2002); *Handbook of Surface and Colloidal Chemistry* (Birdi, K. S., ed, CRC Press, 1997) and *Seymour/Carraher's Polymer Chemistry,* 5th ed. (Marcel Dekker Inc., 2000).

All publications, patents and patent applications cited herein, whether supra or infra, are hereby incorporated by reference in their entirety.

As used in this specification and any appended claims, the singular forms "a," "an" and "the" include plural references unless the content clearly dictates otherwise. Thus, for example, the term "nanoparticle" refers to one or more nanoparticles, and the like.

Unless stated otherwise or unless the context clearly dictates otherwise, all percentages and ratios herein are given on a weight basis.

A. Definitions

In describing the present invention, the following terms will be employed, and are intended to be defined as indicated below.

The term "nanoparticle" as used herein, refers to a particle of less than 1,000 nm in diameter. The nanoparticles within the compositions of the present invention typically have a size distribution in which the Z average and/or the $D(v,0.5)$ value is less than 250 nm, and more typically less than 150 nm and in which the Z average and/or $D(v,0.9)$ is less than 350 nm, and more typically less than 200 nm.

Particle size can be determined (measured) using methods available in the art. For example, particle size can be determined using photon correlation spectroscopy, dynamic light scattering or quasi-elastic light scattering. These methods are based on the correlation of particle size with diffusion properties of particles obtained from Brownian motion measurements. Brownian motion is the random movement of the particles due to bombardment by the solvent molecules that surround the particles. The larger the particle, the more slowly the Brownian motion will be. Velocity is defined by the translational diffusion coefficient (D). The value measured refers to how a particle moves within a liquid (hydrodynamic diameter). The diameter that is obtained is the diameter of a sphere that has the same translational diffusion coefficient as the particle.

Particle size can also be determined using static light scattering, which measures the intensity of light scattered by particles in a solution at a single time. Static light scattering measures light intensity as a function of scattering angle and solute concentration. Particles passing though a light source, for example, a laser beam, scatter light at an angle that is inversely proportional to their size. Large particles generate a diffraction pattern at low scattering angles with high intensity, whereas small particles give rise to wide angle low intensity signals. Particle size distributions can be calculated if the intensity of light scattered from a sample are measured as a function of angle. The angular information is compared with a scattering model (e.g., Mie theory) in order to calculate the size distribution.

Generally, particle size is determined at room temperature and involves multiple analyses of the sample in question (e.g., at least 3 repeat measurements on the same sample) to yield an average value for the particle diameter.

For photon correlation spectroscopy, Z average (also called the cumulant mean or hydrodynamic diameter) is typically calculated from cumulants (monomodal) analysis.

For static light scattering measurements (and also for photon correlation spectroscopy in some embodiments), volume-based size parameters may be measured. For instance, the $D(v,0.5)$ (where v means volume) is a size parameter whose value is defined as the point where 50% of the particles (volume basis) in the composition, as measured, have a size that is less than the $D(v,0.5)$ value, and 50% of the particles in the composition have a size that is greater than the $D(v,0.5)$ value. Similarly, the $D(v,0.9)$ is a size parameter whose value is defined as the point where 90% (volume basis) of the particles in the composition have a size that is less than the $D(v,0.9)$ value, and 10% of the particles in the composition have a size that is greater than the $D(v,0.9)$ value.

As defined herein, a "nanoparticle suspension" is a liquid phase that contains nanoparticles. An "aqueous solution" is a water-containing solution, typically a solution containing more than 50 wt % water, for example, from 50 to 75 to 90 to 95 wt % or more water. An "aqueous nanoparticle suspension" is a water-containing liquid phase that contains nanoparticles. Aqueous nanoparticle suspensions in accordance with the invention typically contain more than 50 wt % water, for example from 50 to 75 to 90 to 95 wt % or more water.

Nanoparticles for use herein are typically formed from polymers that are sterilizable, substantially non-toxic and biodegradable. Such materials include poly($\alpha$-hydroxy acids), polyhydroxybutyric acids, polycaprolactones, polyorthoesters, polyanhydrides, and polycyanoacrylates (e.g., polyalkylcyanoacrylate or "PACA"). More typically, nanoparticles for use with the present invention are polymer nanoparticles derived from poly($\alpha$-hydroxy acids), for example, from a poly(lactide) ("PLA") such as poly(D,L-lactide), a copolymer of lactide and glycolide, such as a poly(D,L-lactide-co-glycolide) ("PLG"), or a copolymer of D,L-lactide and caprolactone. The polymer nanoparticles may be derived from any of various polymeric starting materials which have a variety of molecular weights and, in the case of the copolymers, such as PLG, a variety of monomer (e.g., lactide:glycolide) ratios, the selection of which will be largely a matter of choice, depending in part on the coadministered species. These parameters are discussed further below.

The term "surfactant" comes from the phrase "surface active agent". Surfactants accumulate at interfaces (e.g., at liquid-liquid, liquid-solid and/or liquid-gas interfaces) and change the properties of that interface. As used herein, surfactants include detergents, dispersing agents, suspending agents, emulsion stabilizers, and the like.

As defined herein, "carbohydrates" include monosaccharides, oligosaccharides and polysaccharides, as well as substances derived from monosaccharides, for example, by reduction (e.g., alditols), by oxidation of one or more terminal groups to carboxylic acids (e.g., glucuronic acid), or by replacement of one or more hydroxy group(s) by a hydrogen atom or an amino group (e.g., beta-D-glucosamine and beta-D-galactosamine).

As defined herein, a "monosaccharide" is a polyhydric alcohol, i.e., an alcohol that further comprises either an aldehyde group (in which case the monosaccharide is an aldose) or a keto group (in which case the monosaccharide is a ketose). Monosaccharides typically contain from 3-10 carbons. Moreover, monosaccharides commonly have the empirical formula $(CH_2O)_n$ where n is an integer of three or greater, typically 3-10. Examples of 3-6 carbon aldoses include glyceraldehyde, erythrose, threose, ribose, 2-deoxyribose, arabinose, xylose, lyxose, allose, altrose, glucose, mannose, gulose, idose, galactose, and talose. Examples of 3-6 carbon ketoses include dihydroxyacetone, erythrulose, ribulose, xylulose, psicose, fructose, sorbose, and tagatose. Naturally occurring monosaccharides are normally found in the D-isomer form, as opposed to the L-form.

An "oligosaccharide" refers to a relatively short monosaccharide polymer, i.e., one containing from 2 to 30 monosaccharide units. A "polysaccharide" is a monosaccharide polymer that is beyond oligosaccharide length (i.e., one containing more than 30 monosaccharide units). Moreover, as used herein, the term "polysaccharide" also refers to a monosaccharide polymer that contains two or more linked monosaccharides. To avoid ambiguity, the second definition is to be applied at all times, unless there are explicit indications to the contrary. The term "polysaccharide" also includes polysaccharide derivatives, such as amino-functionalized and carboxyl-functionalized polysaccharide derivatives, among many others. Monosaccharides are typically linked by glycosidic linkages. Specific examples include disaccharides (such as sucrose, lactose, trehalose, maltose, gentiobiose and cellobiose), trisaccharides (such as raffinose), tetrasaccharides (such as stachyose), and pentasaccharides (such as verbascose).

As used herein the term "saccharide" encompasses monosaccharides, oligosaccharides and polysaccharides. A "saccharide-containing species" is a molecule, at least a portion of which is a saccharide. Examples include saccharide cryoprotective agents, saccharide antigens, antigens comprising saccharides conjugated to carrier peptides, and so forth.

As used herein, a "cryoprotective agent" is an agent that protects a composition from experiencing adverse effects upon freezing and thawing. For example, in the present invention, cryoprotective agents may be added to prevent substantial nanoparticle agglomeration from occurring when the lyophilized compositions of the invention are resuspended.

A "polynucleotide" is a nucleic acid polymer. As used herein, a "polynucleotide" can include as few as 5, 6, 7 or 8 nucleotides.

Furthermore, a "polynucleotide" can include both double- and single-stranded sequences and refers to, but is not limited to, cDNA from viral, procaryotic or eucaryotic mRNA, genomic RNA and DNA sequences from viral (e.g. RNA and DNA viruses and retroviruses) or procaryotic DNA, and synthetic DNA sequences. The term also captures sequences that include any of the known base analogs of DNA and RNA. The term further includes modifications, such as deletions, additions and substitutions (generally conservative in nature), to a native sequence, for example, where the nucleic acid molecule encodes an antigenic protein. These modifications may be deliberate, as through site-directed mutagenesis, or may be accidental, such as through mutations of hosts that produce antigens.

As defined herein an "oligonucleotide" is a polynucleotide having in the range of 5 to 100 and more preferably 5 to 30 nucleotides in size.

As used herein, the phrase "nucleic acid" refers to DNA, RNA, or chimeras formed therefrom.

A "polynucleotide-containing species" is a molecule, at least a portion of which is a polynucleotide. Examples include RNA vector constructs, DNA vector constructs and so forth.

The terms "polypeptide" and "protein" refer to a polymer of amino acid residues and are not limited to a minimum length of the product. Thus, peptides, oligopeptides, dimers, multimers, and the like, are included within the definition. Both full-length proteins and fragments thereof are encompassed by the definition. The terms also include modifications, such as deletions, additions and substitutions (generally conservative in nature), to a native sequence, for example, such that the protein maintains the ability to elicit an immunological response or have a therapeutic effect on a subject to which the protein is administered.

A "polypeptide-containing species" is a molecule, at least a portion of which is a polypeptide. Examples include polypeptides, proteins including glycoproteins, saccharide antigens conjugated to carrier proteins, and so forth.

The term "pharmaceutical" refers to biologically active compounds such as antibiotics, antiviral agents, growth factors, hormones, antigens and the like.

The term "adjuvant" refers to any substance that assists or modifies the action of a pharmaceutical, including but not limited to immunological adjuvants, which increase or diversify the immune response to an antigen. Hence, immunological adjuvants are compounds that are capable of potentiating an immune response to antigens. Immunological adjuvants can potentiate humoral and/or cellular immunity.

By "antigen" is meant a molecule that contains one or more epitopes capable of stimulating a host's immune system to make a cellular antigen-specific immune response when the antigen is presented, or a humoral antibody response. An antigen may be capable of eliciting a cellular and/or humoral response by itself or when present in combination with another molecule.

An "epitope" is that portion of an antigenic molecule or antigenic complex that determines its immunological specificity. An epitope is within the scope of the present definition of antigen. Commonly, an epitope is a polypeptide or polysaccharide in a naturally occurring antigen. In artificial antigens it can be a low molecular weight substance such as an arsanilic acid derivative. An epitope will react specifically in vivo or in vitro with, for example, homologous antibodies or T lymphocytes. Alternative descriptors are antigenic determinant, antigenic structural grouping and haptenic grouping.

Frequently, an epitope will include between about 5 to 15 amino acids. Epitopes of a given protein can be identified using any number of epitope mapping techniques, well known in the art. See, e.g., *Epitope Mapping Protocols in Methods in Molecular Biology*, Vol. 66 (Glenn E. Morris, Ed., 1996) Humana Press, Totowa, N.J. For example, linear epitopes may be determined by, for example, concurrently synthesizing large numbers of peptides on solid supports, the peptides corresponding to portions of the protein molecule, and reacting the peptides with antibodies while the peptides are still attached to the supports. Such techniques are known in the art and described in, e.g., U.S. Pat. No. 4,708,871; Geysen et al. (1984) (*Proc. Natl. Acad. Sci. USA* 81:3998-4002); Geysen et al. (1986) (*Molec. Immunol.* 23:709-715). Similarly, conformational epitopes are readily identified by determining spatial conformation of amino acids such as by, e.g., x-ray crystallography and two-dimensional nuclear magnetic resonance. See, e.g., *Epitope Mapping Protocols*, supra.

The term "antigen" as used herein denotes both subunit antigens, i.e., antigens which are separate and discrete from a whole organism with which the antigen is associated in nature, as well as killed, attenuated or inactivated bacteria, viruses, parasites or other pathogens or tumor cells. Antibodies such as anti-idiotype antibodies, or fragments thereof, and synthetic peptide mimotopes, which can mimic an antigen or antigenic determinant, are also captured under the definition of antigen as used herein.

Similarly, an oligonucleotide or polynucleotide that expresses an immunogenic protein, or antigenic determinant in vivo, such as in nucleic acid immunization applications, is also included in the definition of antigen herein.

Furthermore, for purposes of the present invention, an "antigen" refers to a protein having modifications, such as deletions, additions and substitutions (generally conservative in nature), to the native sequence, as long as the protein maintains the ability to elicit an immunological response. These modifications may be deliberate, as through site-directed mutagenesis, or may be accidental, such as through mutations of hosts which produce the antigens.

An "immunological response" or "immune response" to an antigen or composition is the development in a subject of a humoral and/or a cellular immune response to molecules present in the composition of interest. For purposes of the present invention, a "humoral immune response" refers to an immune response mediated by antibody molecules, while a "cellular immune response" is one mediated by T-lymphocytes and/or other white blood cells. One important aspect of cellular immunity involves an antigen-specific response by cytolytic T-cells ("CTLs"). CTLs have specificity for peptide antigens that are presented in association with proteins encoded by the major histocompatibility complex (MHC) and expressed on the surfaces of cells. CTLs help induce and promote the intracellular destruction of intracellular microbes, or the lysis of cells infected with such microbes. Another aspect of cellular immunity involves an antigen-specific response by helper T-cells. Helper T-cells act to help stimulate the function, and focus the activity of, nonspecific effector cells against cells displaying peptide antigens in association with MHC molecules on their surface. A "cellular immune response" also refers to the production of cytokines, chemokines and other such molecules produced by activated T-cells and/or other white blood cells, including those derived from CD4+ and CD8+ T-cells.

A composition such as an immunogenic composition or a vaccine that elicits a cellular immune response may serve to sensitize a vertebrate subject by the presentation of antigen in association with MHC molecules at the cell surface. The cell-mediated immune response is directed at, or near, cells presenting antigen at their surface. In addition, antigen-specific T-lymphocytes can be generated to allow for the future protection of an immunized host.

The ability of a particular antigen or composition to stimulate a cell-mediated immunological response may be determined by a number of assays known in the art, such as by lymphoproliferation (lymphocyte activation) assays, CTL cytotoxic cell assays, by assaying for T-lymphocytes specific for the antigen in a sensitized subject, or by measurement of cytokine production by T cells in response to restimulation with antigen. Such assays are well known in the art. See, e.g., Erickson et al. (1993) (*J. Immunol.* 151:4189-4199); Doe et al. (1994) (*Eur. J. Immunol.* 24:2369-2376); and the examples below.

Hence, an immunological response may include, for example, one or more of the following effects: the production of antibodies by B-cells; and/or the activation of suppressor T-cells and/or γδ T-cells directed specifically to an antigen or antigens present in the composition or vaccine of interest. These responses may serve to neutralize infectivity, and/or mediate antibody-complement, or antibody dependent cell cytotoxicity (ADCC) to provide protection to an immunized host. Such responses can be determined using standard immunoassays and neutralization assays, well known in the art, for instance, radioimmunoassays and ELISAs.

The immunogenic compositions of the present invention display "enhanced immunogenicity" when they possess a greater capacity to elicit an immune response than the immune response elicited by an equivalent amount of the antigen in a differing composition. Thus, a composition may display "enhanced immunogenicity," for example, because the composition generates a stronger immune response, or because a lower dose of antigen is necessary to achieve an immune response in the subject to which it is administered. Such enhanced immunogenicity can be determined, for example, by administering the compositions of the invention, and antigen controls, to animals and comparing assay results of the two.

As used herein, "treatment" (including variations thereof, for example, "treat" or "treated") refers to any of (i) the prevention of a pathogen or disorder in question (e.g. cancer or a pathogenic infection, as in a traditional vaccine), (ii) the reduction or elimination of symptoms, and (iii) the substantial or complete elimination of the pathogen or disorder in question. Treatment may be effected prophylactically (prior to arrival of the pathogen or disorder in question) or therapeutically (following arrival of the same).

The terms "effective amount" or "pharmaceutically effective amount" of an immunogenic composition of the present invention refer herein to a sufficient amount of the immunogenic composition to treat or diagnose a condition of interest. The exact amount required will vary from subject to subject, depending, for example, on the species, age, and general condition of the subject; the severity of the condition being treated; the particular antigen of interest; in the case of an immunological response, the capacity of the subject's immune system to synthesize antibodies, for example, and the degree of protection desired; and the mode of administration, among other factors. An appropriate "effective" amount in any individual case may be determined by one of ordinary skill in the art. Thus, a "therapeutically effective amount" will typically fall in a relatively broad range that can be determined through routine trials.

By "vertebrate subject" or "vertebrate animal" is meant any member of the subphylum cordata, including, without limitation, mammals such as cattle, sheep, pigs, goats, horses, and humans; domestic animals such as dogs and cats; and birds, including domestic, wild and game birds such as cocks and hens including chickens, turkeys and other gallinaceous birds. The term does not denote a particular age. Thus, both adult and newborn animals are covered.

By "pharmaceutically acceptable" or "pharmacologically acceptable" is meant a material which is not biologically or otherwise undesirable, i.e., the material may be administered to an individual without causing any excessively undesirable biological effects in the individual or interacting in an excessively deleterious manner with any of the components of the composition in which it is contained.

The term "excipient" refers to any essentially accessory substance that may be present in the finished dosage form. For example, the term "excipient" includes vehicles, binders, disintegrants, fillers (diluents), lubricants, glidants (flow enhancers), compression aids, colors, sweeteners, preservatives, suspending/dispersing agents, film formers/coatings, flavors and printing inks.

By "physiological pH" or a "pH in the physiological range" is meant a pH in the range of approximately 7.2 to 8.0 inclusive, more typically in the range of approximately 7.2 to 7.6 inclusive.

As used herein, the phrase "vector construct" generally refers to any assembly that is capable of directing the expression of a nucleic acid sequence(s) or gene(s) of interest. A vector construct typically includes transcriptional promoter/enhancer or locus defining element(s), or other elements which control gene expression by other means such as alternate splicing, nuclear RNA export, post-translational modification of messenger, or post-transcriptional modification of protein. In addition, the vector construct typically includes a sequence which, when transcribed, is operably linked to the sequence(s) or gene(s) of interest and acts as a translation initiation sequence. The vector construct may also optionally include a signal that directs polyadenylation, a selectable marker, as well as one or more restriction sites and a translation termination sequence. In addition, if the vector construct is placed into a retrovirus, the vector construct may include a packaging signal, long terminal repeats (LTRs), and positive and negative strand primer binding sites appropriate to the retrovirus used (if these are not already present).

A "DNA vector construct" refers to a DNA molecule that is capable of directing the expression of a nucleic acid sequence(s) or gene(s) of interest.

One specific type of DNA vector construct is a plasmid, which is a circular episomal DNA molecule capable of autonomous replication within a host cell. Typically, a plasmid is a circular double stranded DNA, loop into which additional DNA segments can be ligated. pCMV is one specific plasmid that is well known in the art. A preferred pCMV vector contains the immediate-early enhancer/promoter of CMV and a bovine growth hormone terminator. A specific example is described in detail in Chapman, B. S., et al. (1991) (*Nucleic Acids Res.* 19:3979-3986).

Other DNA vector constructs are known, which are based on RNA viruses. These DNA vector constructs typically comprise a promoter that functions in a eukaryotic cell, 5' of a cDNA sequence for which the transcription product is an RNA vector construct (e.g., an alphavirus RNA vector replicon), and a 3' termination region. The RNA vector construct preferably comprises an RNA genome from a picornavirus, togavirus, flavivirus, coronavirus, paramyxovirus, yellow fever virus, or alphavirus (e.g., Sindbis virus, Semliki Forest virus, Venezuelan equine encephalitis virus, or Ross River virus), which has been modified by the replacement of one or more structural protein genes with a selected heterologous nucleic acid sequence encoding a product of interest. The RNA vector constructs can be obtained by transcription in vitro from a DNA template. Specific examples include Sindbis-virus-based plasmids (pSIN) such as pSINCP, described, for example, in U.S. Pat. Nos. 5,814,482 and 6,015,686, as well as in International Publication Nos. WO 97/38087, WO 99/18226 and WO 02/26209. The construction of such vectors, in general, is described in U.S. Pat. Nos. 5,814,482 and 6,015,686.

Other examples of vector constructs include RNA vector constructs (e.g., alphavirus vector constructs) and the like. As used herein, "RNA vector construct", "RNA vector replicon" and "replicon" refer to an RNA molecule that is capable of directing its own amplification or self-replication in vivo, typically within a target cell. The RNA vector construct is used directly, without the requirement for introduction of DNA into a cell and transport to the nucleus where transcription would occur. By using the RNA vector for direct delivery into the cytoplasm of the host cell, autonomous replication and translation of the heterologous nucleic acid sequence occurs efficiently.

B. General Methods

As indicated above, the nanoparticle compositions of the present invention contain one or more biodegradable polymers, one or more surfactants, one or more cryoprotective agents, one or more antigens and, optionally, one or more supplemental components, for example, one or more immunological adjuvants, among others.

1. Nanoparticle Compositions

Useful polymers for forming the immunogenic nanoparticle compositions described herein include homopolymers, copolymers and polymer blends, both natural and synthetic. Such polymers may be derived, for example, from the following: polyhydroxybutyric acid (also known as polyhydroxybutyrate); polyhydroxy valeric acid (also known as polyhydroxyvalerate); polyglycolic acid (PGA) (also known as polyglycolide); polylactic acid (PLA) (also known as polylactide); polydioxanone; polycaprolactone; polyorthoester; polycyanoacrylates, polyanhydrides; and combinations thereof. More typical are poly($\alpha$-hydroxy acids), such as poly(L-lactide), poly(D,L-lactide) (both referred to as PLA herein), poly(hydroxybutyrates), copolymers of lactide and glycolide, such as poly(D,L-lactide-co-glycolides) (designated as "PLG" herein) or copolymers of D,L-lactide and caprolactone.

The above polymers are available in a variety of molecular weights, and the appropriate molecular weight for a given use is readily determined by one of skill in the art. Thus, for example, a suitable molecular weight for PLA may be on the order of about 2,000 to 5,000. A suitable molecular weight for PLG may range from about 5,000 to about 200,000.

Where copolymers are employed, copolymers with a variety of monomer ratios may be available. For example, where PLG is used to form the nanoparticles, a variety of lactide:glycolide molar ratios will find use herein, and the ratio is largely a matter of choice, depending in part on any coadministered adsorbed and/or entrapped species and the rate of degradation desired. For example, a 50:50 PLG polymer, containing 50% D,L-lactide and 50% glycolide, will provide a faster resorbing copolymer, while 75:25 PLG degrades more slowly, and 85:15 and 90:10, even more slowly, due to the increased lactide component. Mixtures of nanoparticles with varying lactide:glycolide ratios may also find use herein in order to achieve the desired release kinetics. Degradation rate of the nanoparticles of the present invention can also be controlled by such factors as polymer molecular weight and polymer crystallinity.

Where used PLG copolymers are typically those having a lactide/glycolide molar ratio ranging, for example, from 20:80 to 25:75 to 40:60 to 45:55 to 55:45 to 60:40 to 75:25 to 80:20, and having a molecular weight ranging, for example, from 5,000 to 10,000 to 20,000 to 40,000 to 50,000 to 70,000 to 100,000 to 200,00 Daltons, among others.

PLG copolymers with varying lactide:glycolide ratios and molecular weights are readily available commercially from a number of sources including from Boehringer Ingelheim, Germany and Birmingham Polymers, Inc., Birmingham, Ala., USA. Some exemplary PLG copolymers include: (a) RG 502, a PLG having a 50:50 lactide/glycolide molar ratio and a molecular weight of 12,000 Da; (b) RG 503, a PLG having a 50:50 lactide/glycolide molar ratio and a molecular weight of about 34,000 Da; (c) RG 504, a PLG having a 50:50 lactide/glycolide molar ratio and a molecular weight of about 48,000 Da, (d) RG 752, a PLG having a 75:25 lactide/glycolide molar ratio and a molecular weight of about 22,000 Da;

and (e) RG 755, a PLG having a 75:25 lactide/glycolide molar ratio and a molecular weight of about 68,000 Da. PLG polymers can also be synthesized by simple polycondensation of the lactic acid component using techniques well known in the art, such as described in Tabata et al. (1988) (*J. Biomed Mater. Res.* 22:837-858).

Nanoparticles in accordance with the invention can be prepared using any suitable method.

For example, the nanoprecipitation method, also referred to as the solvent displacement method, is one example of a suitable method for forming nanoparticles for use in the invention. See, e.g., European Patent No. 0274961B1 entitled "Process for the preparation of dispersible colloidal systems of a substance in the form of nanocapsules," Devissaguet et al., U.S. Pat. No. 5,049,322 by the same title, and Fessi et al., U.S. Pat. No. 5,118,528, "Process for the preparation of dispersible colloidal systems of a substance in the form of nanoparticles."

As adapted for the present invention, a polymer is dissolved in an organic solvent (e.g., hydrophilic organic solvents such as acetone, ethanol, etc.). The resulting organic solution is combined with a further solvent, which is miscible with the organic solvent while being a non-solvent for the polymer, typically an aqueous solution. The aqueous solution can be, for example, deionized water, normal saline, a buffered solution, such as for example, phosphate-buffered saline (PBS) or a sodium citrate/ethylenediaminetetraacetic acid (sodium citrate/EDTA) buffer solution. The latter solutions can (a) provide a tonicity, i.e., osmolality, that is essentially the same as normal physiological fluids and (b) maintain a pH compatible with normal physiological conditions. In a particular embodiment, the tonicity and/or pH characteristics of the compositions of the present invention can be adjusted after nanoparticle formation.

The organic solution and aqueous solution are then combined in suitable relative volumes (e.g. 1:10 to 1:5 to 1:2 to 1:1 to 2:1 to 5:1 to 10:1, typically from 1:2 to 2:1, more typically about 1:1). For example, the organic solution may be poured or injected into the non-solvent while stirring, or vice versa. By selecting a system in which the polymer is soluble in the organic solvent, while being significantly less soluble in the miscible blend of the organic solvent with the non-solvent, a suspension of nanoparticles may be formed virtually instantaneously. Subsequently, the organic solvent can be eliminated from the suspension, for example, by evaporation under ambient conditions or evaporation under reduced pressure and/or elevated temperature.

The organic solution, the aqueous solution, or both can also contain various other species as desired. For example, in some embodiments, it is desirable to entrap one or more additional species within the nanoparticles or to provide one or more additional species at the particle-fluid interface. Such additional species can include, for instance, antigens, surfactants, cryoprotective agents, immunological adjuvants, and so forth. These species are typically added (a) to the organic solution, if in oil-soluble or oil-dispersible form or (b) to the aqueous solution, if in water-soluble or water-dispersible form.

In some embodiments, one or more additional species are added subsequent to nanoparticle formation (and typically subsequent to organic solvent removal, as well as subsequent to washing steps, if any). For example, agents to adjust tonicity or pH, antigens, surfactants, cryoprotective agents, immunological adjuvants, and so forth, can be added. Frequently, these additional species are added to the nanoparticles as an aqueous solution or dispersion. These species can be, for instance, in solution or accumulate at the particle-solution interface, for example, adsorbed at the nanoparticle surface (see, e.g., the Examples below in which various antigens are adsorbed to the nanoparticle surface). The adsorbed species content can be determined using standard techniques.

Once a suspension of the desired composition is provided, it may be used as is or lyophilized for future use.

Compositions in accordance with the invention can be sterile filtered after nanoparticle formation. For example, compositions can be sterile filtered at any time after nanoparticle formation, such as for example, after nanoparticle formation but before adsorption of any immunological species (e.g., an immunological adjuvant and/or antigen), after adsorption of any immunological species and prior to lyophilization, and so forth.

In general, the microparticles within the compositions, both before and after lyophilization, have a Z average and/or a D(v,0.5) size of less than 250 nm, for example ranging from 250 nm to 200 nm to 150 nm to 100 nm or less.

Taking nanoparticles formed using PLG as an example, there are several advantages of the techniques of the present invention, as compared with microparticle forming techniques (e.g., those described in references cited in the Background section supra and in Singh, M., et al. (2004) (*J. Pharm. Sci.* 93(2):273-282)). A first benefit is the ease of preparation. The nanoparticle method is a single step technique and does not need high-shear homogenization, only magnetic stirring. In addition, the entire microparticle particle preparation process is typically aseptic, whereas, due to their small size, nanoparticles may be sterile filtered post particle preparation, leading to less strict production requirements.

Furthermore, the type of organic solvent used with the two methods is different. The nanoparticle method can be performed using acetone whereas the microparticle method typically involves the use of dichloromethane (DCM) as a solvent. The U.S. Food and Drug Administration (FDA) classifies DCM as a Class 2 solvent and has established limits on the amounts of allowable residual solvent which may be present in pharmaceutical products, whereas acetone is a Class 3 solvent for which the FDA has established higher limits on the allowable amounts.

2. Surfactants

As noted above surfactants for use in the invention include detergents, dispersing agents, suspending agents, emulsion stabilizers, and the like.

Surfactants include cationic, anionic and nonionic surfactants. Cationic surfactants include, for example, cetyltrimethylammonium bromide or "CTAB" (e.g., cetrimide), benzalkonium chloride, DDA (dimethyl dioctodecyl ammonium bromide), and DOTAP (dioleoyl-3-trimethylammonium-propane), among others. Anionic surfactants include, for example, SDS (sodium dodecyl sulfate), SLS (sodium lauryl sulfate), DSS (disulfosuccinate), and sulphated fatty alcohols, among others. Nonionic surfactants include, for example, PVA (polyvinyl alcohol), povidone (also known as polyvinylpyrrolidone or PVP), sorbitan esters, polysorbates, polyoxyethylated glycol monoethers, polyoxyethylated alkyl phenols, and poloxamers, among others.

Compositions in accordance with the invention may contain widely varying amounts of surfactant. Generally, the amount of surfactant will be effective to promote acceptable nanoparticle suspension (and resuspension after lyophilization). The weight ratio of the surfactant to the biodegradable polymer may range, for example, from less than 0.001:1 to 0.5:1 or more, for example, from 0.005:1 to 0.1:1, among other ratios. In general ionic surfactants are used in lower ratios than nonionic surfactants.

3. Cryoprotective Agents

As noted above, cryoprotective agents can be added to the compositions of the present invention to prevent substantial nanoparticle agglomeration from occurring when lyophilized compositions in accordance with the invention are resuspended.

Common cryoprotective agents include (a) amino acids such as glutamic acid and arginine, among others; (b) polyols, including diols such as ethylene glycol, propanediols such as 1,2-propylene glycol and 1,3-propylene glycol, and butane diols such as 2,3-butylene glycol, among others, triols such as glycerol, among others, as well as other higher polyols; and (c) carbohydrates including, for example, (i) monosaccharides (e.g., glucose, galactose, and fructose, among others), (ii) polysaccharides including disaccharides (e.g., sucrose, lactose, trehalose, maltose, gentiobiose and cellobiose, among others), trisaccharides (e.g., raffinose, among others), tetrasaccharides (e.g., stachyose among others), pentasaccharides (e.g., verbascose among others), as well as numerous other higher polysaccharides, and (iii) alditols such as xylitol, sorbitol, and mannitol, among others (in this regard, is noted that alditols are higher polyols, as well as being carbohydrates).

Compositions in accordance with the invention can contain widely varying amounts of cryoprotective agent, depending on the amount that is effective to prevent substantial nanoparticle agglomeration from occurring when the lyophilized compositions of the invention are resuspended. The weight ratio of the surfactant to the biodegradable polymer may range, for example, from less than 0.01:1 to 0.5:1 or more, for example, from 0.05:1 to 0.1:1, among other ratios.

4. Antigens

Compositions of the invention include one or more antigens, each antigen in an effective amount (e.g., an amount effective for use in therapeutic, prophylactic, or diagnostic methods in accordance with the invention). For example, the compositions of the present invention may be used to treat or prevent infections caused by any of the below-listed pathogens.

Antigens for use with the invention include, but are not limited to, one or more of the following antigens set forth below, or antigens derived from one or more of the pathogens set forth below:

A. Bacterial Antigens

Bacterial antigens suitable for use in the invention include proteins, polysaccharides, lipopolysaccharides, and outer membrane vesicles which may be isolated, purified or derived from a bacterium. In addition, bacterial antigens include bacterial lysates and inactivated bacteria formulations. Bacteria antigens can be produced by recombinant expression. Bacterial antigens preferably include epitopes which are exposed on the surface of the bacteria during at least one stage of its life cycle. Bacterial antigens are preferably conserved across multiple serotypes. Bacterial antigens include antigens derived from one or more of the bacteria set forth below as well as the specific antigens examples identified below.

*Neisseria meningitides:* Meningitides antigens include proteins (such as those identified in WO99/24578; WO99/36544; WO99/57280; WO00/22430; Tettelin et al. (2000) *Science* 287:1809-1815; WO96/29412; and Pizza et al. (2000) *Science* 287:1816-1820), saccharides (including a polysaccharide, oligosaccharide or lipopolysaccharide), or outer-membrane vesicles (WO 01/52885; Bjune et al. (1991) *Lancet* 338(8775):1093-1096; Fuskasawa et al. (1999) *Vaccine* 17:2951-2958; and Rosenqist et al. (1998) *Dev. Biol. Strand* 92:323-333) purified or derived from *N. meningitides* serogroup such as A, C, W135, Y, and/or B. Meningitides protein antigens can be selected from adhesions, autotransporters, toxins, Fe acquisition proteins, and membrane associated proteins (preferably integral outer membrane protein).

*Streptococcus pneumoniae: Streptococcus pneumoniae* antigens include a saccharide (including a polysaccharide or an oligosaccharide) and/or protein from *Streptococcus pneumoniae*. Saccharide antigens can be selected from serotypes 1, 2, 3, 4, 5, 6B, 7F, 8, 9N, 9V, 10A, 11A, 12F, 14, 15B, 17F, 18C, 19A, 19F, 20, 22F, 23F, and 33F. Protein antigens can be selected from a protein identified in WO 98/18931; WO 98/18930; U.S. Pat. Nos. 6,699,703; 6,800,744; WO 97/43303; and WO 97/37026. *Streptococcus pneumoniae* proteins can be selected from the Poly Histidine Triad family (PhtX), the Choline Binding Protein family (CbpX), CbpX truncates, LytX family, LytX truncates, CbpX truncate-LytX truncate chimeric proteins, pneumolysin (Ply), PspA, PsaA, Sp128, Sp101, Sp130, Sp125 or Sp133.

*Streptococcus pyogenes* (Group A *Streptococcus*): Group A *Streptococcus* antigens include proteins identified in WO 02/34771 and WO 2005/032582 (including GAS 40), fusions of fragments of GAS M proteins (including those described in WO 02/094851; and Dale (1999) *Vaccine* 17:193-200, and Dale (1996) *Vaccine* 14(10): 944-948), fibronectin binding protein (Sfb1), Streptococcal heme-associated protein (Shp), and Streptolysin S (SagA).

*Moraxella catarrhalis: Moraxella* antigens include antigens identified in WO 02/18595; and WO 99/58562, outer membrane protein antigens (HMW-OMP), C-antigen, and/or LPS.

*Bordetella pertussis:* Pertussis antigens include petussis holotoxin (PT) and filamentous haemagglutinin (FHA) from *B. pertussis*, optionally also combination with pertactin and/or agglutinogens 2 and 3 antigen.

*Staphylococcus aureus:* Staph aureus antigens include *S. aureus* type 5 and 8 capsular polysaccharides optionally conjugated to nontoxic recombinant *Pseudomonas aeruginosa* exotoxin A, such as StaphVAX™, and antigens derived from surface proteins, invasins (leukocidin, kinases, hyaluronidase), surface factors that inhibit phagocytic engulfment (capsule, Protein A), carotenoids, catalase production, Protein A, coagulase, clotting factor, and membrane-damaging toxins (optionally detoxified) that lyse eukaryotic cell membranes (hemolysins, leukotoxin, leukocidin).

*Staphylococcus epidermis: S. epidermidis* antigens include slime-associated antigen (SAA).

*Clostridium tetani* (Tetanus): Tetanus antigens include tetanus toxoid (TT), preferably used as a carrier protein in conjunction/conjugated with the compositions of the present invention.

*Cornynebacterium diphtheriae* (Diphtheria): Diphtheria antigens include diphtheria toxin, preferably detoxified, such as $CRM_{197}$. Additionally, antigens capable of modulating, inhibiting or associated with ADP ribosylation are contemplated for combination/co-administration/conjugation with the compositions of the present invention. The diphtheria toxoids may be used as carrier proteins.

*Haemophilus influenzae* B (Hib): Hib antigens include a Hib saccharide antigen.

*Pseudomonas aeruginosa: Pseudomonas* antigens include endotoxin A, Wzz protein, *P. aeruginosa* LPS, more particularly LPS isolated from PAO1 (O5 serotype), and Outer Membrane Proteins, including Outer Membrane Proteins F (OprF) (Price et al. (2001) *Infect Immun.* 69(5):3510-3515).

*Legionella pneumophila*. Bacterial antigens can be derived from *Legionella pneumophila*.

*Streptococcus agalactiae* (Group B *Streptococcus*): Group B *Streptococcus* antigens include protein and saccharide antigens, such as those identified in WO 02/34771; WO 03/093306; WO 04/041157; and WO 2005/002619 (including proteins GBS 59, GBS 67, GBS 80, GBS 104, GBS 276, GBS 322, and including saccharide antigens derived from serotypes Ia, Ib, Ia/c, II, III, IV, V, VI, VII and VIII).

*Neisserria gonorrhoeae*: Gonorrhoeae antigens include Por (or porin) protein, such as PorB (see, e.g., Zhu et al. (2004) *Vaccine* 22:660-669), a transferring binding protein, such as TbpA and TbpB (see, e.g., Price et al. (2004) *Infect. Immun.* 71(1):277-283), an opacity protein (such as Opa), a reduction-modifiable protein (Rmp), and outer membrane vesicle (OMV) preparations (see, e.g., Plante et al. (2000) *J. Infect. Dis.* 182:848-855); WO 99/24578; WO 99/36544; WO 99/57280; and WO02/079243).

*Chlamydia trachomatis*: *Chlamydia trachomatis* antigens include antigens derived from serotypes A, B, Ba and C (agents of trachoma, a cause of blindness), serotypes $L_1$, $L_2$ & $L_3$ (associated with Lymphogranuloma venereum), and serotypes, D-K. *Chlamydia trachomas* antigens also include antigens identified in WO 00/37494; WO 03/049762; WO 03/068811; and WO 05/002619, including PepA (CT045), LcrE (CT089), ArtJ (CT381), DnaK (CT396), CT398, OmpH-like (CT242), L7/L12 (CT316), OmcA (CT444), AtosS (CT467), CT547, Eno (CT587), HrtA (CT823), MurG (CT761), CT396 and CT761, and specific combinations of these antigens.

*Treponema pallidum* (Syphilis): Syphilis antigens include TmpA antigen.

*Haemophilus ducreyi* (causing chancroid): *Ducreyi* antigens include outer membrane protein (DsrA).

*Enterococcus faecalis* or *Enterococcus faecium*: Antigens include a trisaccharide repeat and other *Enterococcus* derived antigens provided in U.S. Pat. No. 6,756,361.

*Helicobacter pylori*: *H pylori* antigens include Cag, Vac, Nap, HopX, HopY and urease antigen.

*Staphylococcus saprophyticus*: Antigens include the 160 kDa hemagglutinin of *S. saprophyticus* antigen.

*Yersinia enterocolitica* Antigens include LPS (Xu et al. (2002) *Infect. Immun.* 70(8): 4414-4423).

*E. coli*: *E. coli* antigens can be derived from enterotoxigenic *E. coli* (ETEC), enteroaggregative *E. coli* (EAggEC), diffusely adhering *E. coli* (DAEC), enteropathogenic *E. coli* (EPEC), or enterohemorrhagic *E. coli* (EHEC).

*Bacillus anthracis* (anthrax): *B. anthracis* antigens are optionally detoxified and can be selected from A-components (lethal factor (LF) and edema factor (EF)), both of which can share a common B-component known as protective antigen (PA). In certain embodiments, the compositions of the present invention do not include an anthrax antigen.

*Yersinia pestis* (plague): Plague antigens include F1 capsular antigen (Gosfeld et al. (2003) *Infect. Immun.* 71(1)): 374-383), LPS (Fields et al., (1999) *Infect. Immun.* 67(10): 5395-5408), *Yersinia pestis* V antigen (Hill et al. (1997) *Infect. Immun.* 65(11): 4476-4482).

*Mycobacterium tuberculosis*: Tuberculosis antigens include lipoproteins, LPS, BCG antigens, a fusion protein of antigen 85B (Ag85B) and ESAT-6 optionally formulated in cationic lipid vesicles (Olsen et al. (2004) *Infect. Immun.* 72(10): 6148-6150), *Mycobacterium tuberculosis* (Mtb) isocitrate dehydrogenase associated antigens (Banerjee et al. (2004) *Proc. Natl. Acad. Sci. USA* 101(34):12652-12657), and MPT51 antigens (Suzuki et al. (2004) *Infect. Immun.* 72(7):3829-3837).

*Rickettsia*: Antigens include outer membrane proteins, including the outer membrane protein A and/or B (OmpB) (Chao et al. (2004) *Biochim. Biophys. Acta.* 1702(2):145-152), LPS, and surface protein antigen (SPA) (Carl et al. (1989) *J. Autoimmun.* 2 Suppl:81-91).

*Listeria monocytogenes*. Bacterial antigens can be derived from *Listeria monocytogenes*.

*Chlamydia pneumoniae*: Antigens include those identified in WO 02/02606 and WO 05/084306, including CPn0324, Cpn0301, Cpn0482, Cpn0503, Cpn0525, Cpn0558, Cpn0584, Cpn0800, Cpn0979, Cpn0498, Cpn0300, Cpn0042, Cpn0013, Cpn450, Cpn0661, Cpn0557, Cpn0904, Clpn0795, Cpn0186 and Cpn0604, and specific combinations of these antigens.

*Vibrio cholerae*: Antigens include proteinase antigens, LPS, particularly lipopolysaccharides of *Vibrio cholerae* II, O1 Inaba O-specific polysaccharides, *V. cholera* O139, antigens of IEM108 vaccine (Liang et al. (2003) *Infect. Immun.* 71(10):5498-5504), and Zonula occludens toxin (Zot).

*Salmonella typhi* (typhoid fever): Antigens include capsular polysaccharides preferably conjugates (Vi, i.e. vax-TyVi).

*Borrelia burgdorferi* (Lyme disease): Antigens include lipoproteins (such as OspA, OspB, Osp C and Osp D), other surface proteins such as OspE-related proteins (Erps), decorin-binding proteins (such as DbpA), and antigenically variable VI proteins, such as antigens associated with P39 and P13 (an integral membrane protein, Noppa et al. (2001) *Infect. Immun.* 69(5):3323-3334), VlsE Antigenic Variation Protein (Lawrenz et al. (1999) *J. Clin. Microbiol.* 37(12): 3997-4004).

*Porphyromonas gingivalis*: Antigens include *P. gingivalis* outer membrane protein (OMP).

*Klebsiella*: Antigens include OMPs, including OMP A, and polysaccharides optionally conjugated to tetanus toxoid.

Other bacterial antigens include capsular antigens, polysaccharide antigens or protein antigens of any of the above. Further bacterial antigens also include outer membrane vesicle (OMV) preparations. Additionally, antigens include live, attenuated, and/or purified versions of any of the aforementioned bacteria. Antigens can be derived from gram-negative or gram-positive bacteria. Antigens can be derived from aerobic or anaerobic bacteria.

Additionally, any of the above bacterial-derived saccharides (polysaccharides, LPS, LOS or oligosaccharides) can be conjugated to another agent or antigen, such as a carrier protein (for example $CRM_{197}$). Such conjugation can be direct conjugation effected by reductive amination of carbonyl moieties on the saccharide to amino groups on the protein, as provided in U.S. Pat. No. 5,360,897; and Roy et al. (1984) *Can. J. Biochem. Cell Biol.* 62(5):270-275. In another embodiment, the saccharides can be conjugated through a linker, such as, with succinamide or other linkages provided in Hermanson, G. T., *Bioconjugate Techniques,* 1st ed., Academic Press (1996) and Wong, S. S., *CRC, Chemistry of Protein Conjugation and Cross-Linking,* 1st ed., CRC-Press (1991).

B. Viral Antigens

Viral antigens suitable for use in the invention include inactivated (or killed) virus, attenuated virus, split virus formulations, purified subunit formulations, viral proteins which may be isolated, purified or derived from a virus, and Virus Like Particles (VLPs). Viral antigens can be derived from viruses propagated on cell culture or other substrate or expressed recombinantly. Viral antigens preferably include epitopes which are exposed on the surface of the virus during at least one stage of its life cycle. Viral antigens are preferably conserved across multiple serotypes or isolates. Viral antigens include antigens derived from one or more of the viruses set forth below as well as the specific antigens examples identified below.

Orthomyxovirus: Viral antigens may be derived from an Orthomyxovirus, such as Influenza A, B and C. Orthomyxovirus antigens may be selected from one or more of the viral proteins, including hemagglutinin (HA), neuraminidase (NA), nucleoprotein (NP), matrix protein (M1), membrane protein (M2), one or more of the transcriptase components (PB1, PB2 and PA). Preferred antigens include HA and NA.

Influenza antigens may be derived from interpandemic (annual) flu strains. Influenza antigens may be derived from strains with the potential to cause pandemic a pandemic outbreak (i.e., influenza strains with new haemagglutinin compared to the haemagglutinin in currently circulating strains, or influenza strains which are pathogenic in avian subjects and have the potential to be transmitted horizontally in the human population, or influenza strains which are pathogenic to humans). Influenza antigens may be derived from viruses grown in eggs or cell culture.

Paramyxoviridae viruses: Viral antigens may be derived from Paramyxoviridae viruses, such as Pneumoviruses (RSV), Paramyxoviruses (PIV) and Morbilliviruses (Measles).

Pneumovirus: Viral antigens may be derived from a Pneumovirus, such as Respiratory syncytial virus (RSV), Bovine respiratory syncytial virus, Pneumonia virus of mice, and Turkey rhinotracheitis virus. Preferably, the Pneumovirus is RSV. Pneumovirus antigens may be selected from one or more of the following proteins, including surface proteins Fusion (F), Glycoprotein (G) and Small Hydrophobic protein (SH), matrix proteins M and M2, nucleocapsid proteins N, P and L and nonstructural proteins NS1 and NS2. Preferred Pneumovirus antigens include F, G and M. See e.g., Johnstone et al. (2004) *J. Gen. Virol.* 85(Pt 11):3229-3238). Pneumovirus antigens may also be formulated in or derived from chimeric viruses. For example, chimeric RSV/PIV viruses may comprise components of both RSV and PIV.

Paramyxovirus: Viral antigens may be derived from a Paramyxovirus, such as Parainfluenza virus types 1-4 (PIV), Mumps, Sendai viruses, Simian virus 5, Bovine parainfluenza virus and Newcastle disease virus. Preferably, the Paramyxovirus is PIV or Mumps. Paramyxovirus antigens may be selected from one or more of the following proteins: Hemagglutinin Neuraminidase (HN), Fusion proteins F1 and F2, Nucleoprotein (NP), Phosphoprotein (P), Large protein (L), and Matrix protein (M). Preferred Paramyxovirus proteins include HN, F1 and F2. Paramyxovirus antigens may also be formulated in or derived from chimeric viruses. For example, chimeric RSV/PIV viruses may comprise components of both RSV and PIV. Commercially available mumps vaccines include live attenuated mumps virus, in either a monovalent form or in combination with measles and rubella vaccines (MMR).

Morbillivirus: Viral antigens may be derived from a Morbillivirus, such as Measles. Morbillivirus antigens may be selected from one or more of the following proteins: hemagglutinin (H), Glycoprotein (G), Fusion factor (F), Large protein (L), Nucleoprotein (NP), Polymerase phosphoprotein (P), and Matrix (M). Commercially available measles vaccines include live attenuated measles virus, typically in combination with mumps and rubella (MMR).

Picornavirus: Viral antigens may be derived from Picornaviruses, such as Enteroviruses, Rhinoviruses, Heparnavirus, Cardioviruses and Aphthoviruses. Antigens derived from Enteroviruses, such as Poliovirus are preferred.

Enterovirus: Viral antigens may be derived from an Enterovirus, such as Poliovirus types 1, 2 or 3, Coxsackie A virus types 1 to 22 and 24, Coxsackie B virus types 1 to 6, Echovirus (ECHO) virus) types 1 to 9, 11 to 27 and 29 to 34 and Enterovirus 68 to 71. Preferably, the Enterovirus is poliovirus. Enterovirus antigens are preferably selected from one or more of the following Capsid proteins VP1, VP2, VP3 and VP4. Commercially available polio vaccines include Inactivated Polio Vaccine (IPV) and Oral poliovirus vaccine (OPV).

Heparnavirus: Viral antigens may be derived from a Heparnavirus, such as Hepatitis A virus (HAV). Commercially available HAV vaccines include inactivated HAV vaccine.

Togavirus: Viral antigens may be derived from a Togavirus, such as a Rubivirus, an Alphavirus, or an Arterivirus. Antigens derived from Rubivirus, such as Rubella virus, are preferred. Togavirus antigens may be selected from E1, E2, E3, C, NSP-1, NSPO-2, NSP-3 and NSP-4. Togavirus antigens are preferably selected from E1, E2 and E3. Commercially available Rubella vaccines include a live cold-adapted virus, typically in combination with mumps and measles vaccines (MMR).

Flavivirus: Viral antigens may be derived from a Flavivirus, such as Tick-borne encephalitis (TBE), Dengue (types 1, 2, 3 or 4), Yellow Fever, Japanese encephalitis, West Nile encephalitis, St. Louis encephalitis, Russian spring-summer encephalitis, Powassan encephalitis. Flavivirus antigens may be selected from PrM, M, C, E, NS-1, NS-2a, NS2b, NS3, NS4a, NS4b, and NS5. Flavivirus antigens are preferably selected from PrM, M and E. Commercially available TBE vaccine include inactivated virus vaccines.

Pestivirus: Viral antigens may be derived from a Pestivirus, such as Bovine viral diarrhea (BVDV), Classical swine fever (CSFV) or Border disease (BDV).

Hepadnavirus: Viral antigens may be derived from a Hepadnavirus, such as Hepatitis B virus. Hepadnavirus antigens may be selected from surface antigens (L, M and S), core antigens (HBc, HBe). Commercially available HBV vaccines include subunit vaccines comprising the surface antigen S protein.

Hepatitis C virus: Viral antigens may be derived from a Hepatitis C virus (HCV). HCV antigens may be selected from one or more of E1, E2, E1/E2, NS345 polyprotein, NS 345-core polyprotein, core, and/or peptides from the nonstructural regions (Houghton et al. (1991) *Hepatology* 14:381-388).

Rhabdovirus: Viral antigens may be derived from a Rhabdovirus, such as a Lyssavirus (Rabies virus) and Vesiculdvirus (VSV). Rhabdovirus antigens may be selected from glycoprotein (G), nucleoprotein (N), large protein (L) and nonstructural proteins (NS). Commercially available Rabies virus vaccine comprise killed virus grown on human diploid cells or fetal rhesus lung cells.

Caliciviridae: Viral antigens may be derived from Caliciviridae, such as Norwalk virus, and Norwalk-like Viruses, such as Hawaii Virus and Snow Mountain Virus.

Coronavirus: Viral antigens may be derived from a Coronavirus, SARS, Human respiratory coronavirus, Avian infectious bronchitis (IBV), Mouse hepatitis virus (MHV), and Porcine transmissible gastroenteritis virus (TGEV). Coronavirus antigens may be selected from spike (S), envelope (E), matrix (M), nucleocapsid (N), and Hemagglutinin-esterase glycoprotein (HE). Preferably, the Coronavirus antigen is derived from a SARS virus. SARS viral antigens are described in WO 04/92360;

Retrovirus: Viral antigens may be derived from a Retrovirus, such as an Oncovirus, a Lentivirus or a Spumavirus. Oncovirus antigens may be derived from HTLV-1, HTLV-2 or HTLV-5. Lentivirus antigens may be derived from HIV-1 or HIV-2. Retrovirus antigens may be selected from gag, pol, env, tax, tat, rex, rev, nef, vif, vpu, and vpr. HIV antigens may be selected from gag (p24gag and p55gag), env (gp160 and gp41), pol, tat, nef, rev vpu, miniproteins, (preferably p55 gag and gp140v delete). HIV antigens may be derived from one or more of the following strains: $HIV_{IIIb}$, $HIV_{SF2}$, $HIV_{LAV}$, $HIV_{LAI}$, $HIV_{MN}$, $HIV-1_{CM235}$, $HIV-1_{US4}$.

Reovirus: Viral antigens may be derived from a Reovirus, such as an Orthoreovirus, a Rotavirus, an Orbivirus, or a Coltivirus. Reovirus antigens may be selected from structural proteins λ1, λ2, λ3, μ1, μ2, σ1, σ2, or σ3, or nonstructural proteins σNS, μNS, or σ1s. Preferred Reovirus antigens may be derived from a Rotavirus. Rotavirus antigens may be selected from VP1, VP2, VP3, VP4 (or the cleaved product VP5 and VP8), NSP 1, VP6, NSP3, NSP2, VP7, NSP4, or NSP5. Preferred Rotavirus antigens include VP4 (or the cleaved product VP5 and VP8), and VP7.

Parvovirus: Viral antigens may be derived from a Parvovirus, such as Parvovirus B19. Parvovirus antigens may be selected from VP-1, VP-2, VP-3, NS-1 and NS-2. Preferably, the Parvovirus antigen is capsid protein VP-2.

Delta hepatitis virus (HMO: Viral antigens may be derived HDV, particularly δ-antigen from HDV (see, e.g., U.S. Pat. No. 5,378,814).

Hepatitis E virus (HEV): Viral antigens may be derived from HEV.

Hepatitis G virus (HGV): Viral antigens may be derived from HGV.

Human Herpesvirus: Viral antigens may be derived from a Human Herpesvirus, such as Herpes Simplex Viruses (HSV), Varicella-zoster virus (VZV), Epstein-Barr virus (EBV), Cytomegalovirus (CMV), Human Herpesvirus 6 (HHV6), Human Herpesvirus 7 (HHV7), and Human Herpesvirus 8 (HHV8). Human Herpesvirus antigens may be selected from immediate early proteins (α), early proteins (β), and late proteins (γ). HSV antigens may be derived from HSV-1 or HSV-2 strains. HSV antigens may be selected from glycoproteins gB, gC, gD and gH, fusion protein (gB), or immune escape proteins (gC, gE, or gI). VZV antigens may be selected from core, nucleocapsid, tegument, or envelope proteins. A live attenuated VZV vaccine is commercially available. EBV antigens may be selected from early antigen (EA) proteins, viral capsid antigen (VCA), and glycoproteins of the membrane antigen (MA). CMV antigens may be selected from capsid proteins, envelope glycoproteins (such as gB and gH), and tegument proteins Papovaviruses: Antigens may be derived from Papovaviruses, such as Papillomaviruses and Polyomaviruses. Papillomaviruses include HPV serotypes 1, 2, 4, 5, 6, 8, 11, 13, 16, 18, 31, 33, 35, 39, 41, 42, 47, 51, 57, 58, 63 and 65. Preferably, HPV antigens are derived from serotypes 6, 11, 16 or 18. HPV antigens may be selected from capsid proteins (L1) and (L2), or E1-E7, or fusions thereof. HPV antigens are preferably formulated into virus-like particles (VLPs). Polyomyavirus viruses include BK virus and JK virus. Polyomavirus antigens may be selected from VP1, VP2 or VP3.

Other antigens, compositions, methods, and microbes for use in the invention are described in Plotkin, S. A. et al., *Vaccines*, 4<sup>th</sup> ed., W.B. Saunders Co. (2004); Murray, P. R. et al., *Medical Microbiology* 5<sup>th</sup> ed., Mosby Elsevier (2005); Joklik, W. K. (ed.), *Virology*, 3rd ed., Appleton & Lange (1988); Howley, P. M. et al. (eds.), *Fundamental Virology*, 4th ed., Lippincott Williams & Wilkins (1991); and Fields, B. N. et al. (eds.), *Fields Virology*, 4th ed., Lippincott Williams & Wilkins (2001).

C. Fungal Antigens

Fungal antigens for use in the invention can be derived from one or more of the fungi set forth below.

Fungal antigens may be derived from Dermatophytres, including: *Epidermophyton floccusum, Microsporum audouini, Microsporum canis, Microsporum distortum, Microsporum equinum, Microsporum gypsum, Microsporum nanum, Trichophyton concentricum, Trichophyton equinum, Trichophyton gallinae, Trichophyton gypseum, Trichophyton megnini, Trichophyton mentagrophytes, Trichophyton quinckeanum, Trichophyton rubrum, Trichophyton schoenleini, Trichophyton tonsurans, Trichophyton verrucosum, T. verrucosum* var. *album*, var. *discoides*, var. *ochraceum, Trichophyton violaceum*, and/or *Trichophyton faviforme*.

Fungal pathogens may be derived from *Aspergillus fumigatus, Aspergillus flavus, Aspergillus niger, Aspergillus nidulans, Aspergillus terreus, Aspergillus sydowi, Aspergillus flavatus, Aspergillus glaucus, Blastoschizomyces capitatus, Candida albicans, Candida enolase, Candida tropicalis, Candida glabrata, Candida krusei, Candida parapsilosis, Candida stellatoidea, Candida kusei, Candida parakwsei, Candida lusitaniae, Candida pseudotropicalis, Candida guilliermondi, Cladosporium carrionii, Coccidioides immitis, Blastomyces dermatidis, Cryptococcus neoformans, Geotrichum clavatum, Histoplasma capsulatum, Klebsiella pneumoniae, Paracoccidioides brasiliensis, Pneumocystis carinii, Pythiumn insidiosum, Pityrosporum ovale, Saccharomyces cerevisae, Saccharomyces boulardii, Saccharomyces pombe, Scedosporium apiosperum, Sporothrix schenckii, Trichosporon beigelii, Toxoplasma gondii, Penicillium marneffei, Malassezia* spp., *Fonsecaea* spp., *Wangiella* spp., *Sporothrix* spp., *Basidiobolus* spp., *Conidiobolus* spp., *Rhizopus* spp, *Mucor* spp, *Absidia* spp, *Mortierella* spp, *Cunninghamella* spp, *Saksenaea* spp., *Alternaria* spp, *Curvularia* spp, *Helminthosporium* spp, *Fusarium* spp, *Aspergillus* spp, *Penicillium* spp, *Monolinia* spp, *Rhizoctonia* spp, *Paecilomyces* spp, *Pithomyces* spp, and *Cladosporium* spp.

Processes for producing fungal antigens are well known in the art (see U.S. Pat. No. 6,333,164). In a preferred method, a solubilized fraction extracted and separated from an insoluble fraction obtainable from fungal cells of which cell wall has been substantially removed or at least partially removed, characterized in that the process comprises the steps of: obtaining living fungal cells; obtaining fungal cells of which cell wall has been substantially removed or at least partially removed; bursting the fungal cells of which cell wall has been substantially removed or at least partially removed; obtaining an insoluble fraction; and extracting and separating a solubilized fraction from the insoluble fraction.

D. STD Antigens

The compositions of the invention can include one or more antigens derived from a sexually transmitted disease (STD). Such antigens can provide for prophylactis or therapy for STDs such as chlamydia, genital herpes, hepatits (such as HCV), genital warts, gonorrhoea, syphilis and/or chancroid (see WO 00/15255). Antigens may be derived from one or more viral or bacterial STDs. Viral STD antigens for use in the invention may be derived from, for example, HIV, herpes simplex virus (HSV-1 and HSV-2), human papillomavirus (HPV), and hepatitis (HCV). Bacterial STD antigens for use in the invention may be derived from, for example, *Neiserria gonorrhoeae, Chlamydia trachomatis, Treponema pallidum, Haemophilus ducreyi, E. coli*, and *Streptococcus agalactiae*. Examples of specific antigens derived from these pathogens are described above.

E. Respiratory Antigens

The compositions of the invention can include one or more antigens derived from a pathogen which causes respiratory disease. For example, respiratory antigens may be derived from a respiratory virus such as Orthomyxoviruses (influenza), Pneumovirus (RSV), Paramyxovirus (PIV), Morbillivirus (measles), Togavirus (Rubella), VZV, and Coronavirus (SARS). Respiratory antigens may be derived from a bacterium which causes respiratory disease, such as *Streptococcus pneumoniae, Pseudomonas aeruginosa, Bordetella pertussis, Mycobacterium tuberculosis, Mycoplasma pneumoniae, Chlamydia pneumoniae, Bacillus anthracis*, and *Moraxella catarrhalis*. Examples of specific antigens derived from these pathogens are described above.

F. Pediatric Vaccine Antigens

The compositions of the invention may include one or more antigens suitable for use in pediatric subjects. Pediatric subjects are typically less than about 3 years old, or less than about 2 years old, or less than about 1 years old. Pediatric antigens can be administered multiple times over the course of 6 months, 1, 2 or 3 years. Pediatric antigens may be derived from a virus which may target pediatric populations and/or a virus from which pediatric populations are susceptible to infection. Pediatric viral antigens include antigens derived from one or more of Orthomyxovirus (influenza), Pneumovirus (RSV), Paramyxovirus (PIV and Mumps), Morbillivirus (measles), Togavirus (Rubella), Enterovirus (polio), HBV, Coronavirus (SARS), and Varicella-zoster virus (VZV), Epstein Barr virus (EBV). Pediatric bacterial antigens include antigens derived from one or more of *Streptococcus pneumoniae, Neisseria meningitides, Streptococcus pyogenes* (Group A *Streptococcus*), *Moraxella catarrhalis, Bordetella pertussis, Staphylococcus aureus, Clostridium tetani* (Tetanus), *Corynebacterium diphtheriae* (Diphtheria), *Haemophilus influenzae* B (Hib), *Pseudomonas aeruginosa, Streptococcus agalactiae* (Group B *Streptococcus*), and *E. coli*. Examples of specific antigens derived from these pathogens are described above.

G. Antigens Suitable for Use in Elderly or Immunocompromised Individuals

The compositions of the invention can include one or more antigens suitable for use in elderly or immunocompromised individuals. Such individuals may need to be vaccinated more frequently, with higher doses or with adjuvanted formulations to improve their immune response to the targeted antigens. Antigens which may be targeted for use in elderly or immunocompromised individuals include antigens derived from one or more of the following pathogens: *Neisseria meningitides, Streptococcus pneumoniae, Streptococcus pyogenes* (Group A *Streptococcus*), *Moraxella catarrhalis, Bordetella pertussis, Staphylococcus aureus, Staphylococcus epidermis, Clostridium tetani* (Tetanus), *Corynebacterium diphtheriae* (Diphtheria), *Haemophilus influenzae* B (Hib), *Pseudomonas aeruginosa, Legionella pneumophila, Streptococcus agalactiae* (Group B *Streptococcus*), *Enterococcus faecalis, Helicobacter pylori, Clamydia pneumoniae*, Orthomyxovirus (influenza), Pneumovirus (RSV), Paramyxovirus (PIV and Mumps), Morbillivirus (measles), Togavirus (Rubella), Enterovirus (polio), HBV, Coronavirus (SARS), Varicellazoster virus (VZV), Epstein Barr virus (EBV), Cytomegalovirus (CMV). Examples of specific antigens derived from these pathogens are described above.

H. Antigens Suitable for Use in Adolescent Vaccines

The compositions of the invention can include one or more antigens suitable for use in adolescent subjects. Adolescents may be in need of a boost of a previously administered pediatric antigen. Pediatric antigens which may be suitable for use in adolescents are described above. In addition, adolescents may be targeted to receive antigens derived from an STD pathogen in order to ensure protective or therapeutic immunity before the beginning of sexual activity. STD antigens which may be suitable for use in adolescents are described above.

I. Tumor Antigens

The compositions of the invention can include one or more tumor or cancer antigens. Tumor antigens can be, for example, peptide-containing tumor antigens, such as a polypeptide tumor antigen or glycoprotein tumor antigens. A tumor antigen can also be, for example, a saccharide-containing tumor antigen, such as a glycolipid tumor antigen or a ganglioside tumor antigen. A tumor antigen can further be, for example, a polynucleotide-containing tumor antigen that expresses a polypeptide-containing tumor antigen, for instance, an RNA vector construct or a DNA vector construct, such as plasmid DNA.

Tumor antigens include (a) polypeptide-containing tumor antigens, including polypeptides (which can range, for example, from 8-20 amino acids in length, although lengths outside this range are also common), lipopolypeptides and glycoproteins, (b) saccharide-containing tumor antigens, including poly-saccharides, mucins, gangliosides, glycolipids and glycoproteins, and (c) polynucleotides that express antigenic polypeptides.

Tumor antigens can be, for example, (a) full length molecules associated with cancer cells, (b) homologs and modified forms of the same, including molecules with deleted, added and/or substituted portions, and (c) fragments of the same. Tumor antigens can be provided in recombinant form. Tumor antigens include, for example, class I-restricted antigens recognized by CD8+ lymphocytes or class II-restricted antigens recognized by CD4+ lymphocytes.

Numerous tumor antigens are known in the art, including: (a) cancer-testis antigens such as NY-ESO-1, SSX2, SCP1 as well as RAGE, BAGE, GAGE and MAGE family polypeptides, for example, GAGE-1, GAGE-2, MAGE-1, MAGE-2, MAGE-3, MAGE-4, MAGE-5, MAGE-6, and MAGE-12 (which can be used, for example, to address melanoma, lung, head and neck, NSCLC, breast, gastrointestinal, and bladder tumors), (b) mutated antigens, for example, p53 (associated with various solid tumors, e.g., colorectal, lung, head and neck cancer), p21/Ras (associated with, e.g., melanoma, pancreatic cancer and colorectal cancer), CDK4 (associated with, e.g., melanoma), MUM1 (associated with, e.g., melanoma), caspase-8 (associated with, e.g., head and neck cancer), CIA 0205 (associated with, e.g., bladder cancer), HLA-A2-R1701, beta catenin (associated with, e.g., melanoma), TCR (associated with, e.g., T-cell non-Hodgkins lymphoma), BCR-abl (associated with, e.g., chronic myelogenous leukemia), triosephosphate isomerase, KIA 0205, CDC-27, and LDLR-FUT, (c) over-expressed antigens, for example, Galectin 4 (associated with, e.g., colorectal cancer), Galectin 9 (associated with, e.g., Hodgkin's disease), proteinase 3 (associated with, e.g., chronic myelogenous leukemia), WT 1 (associated with, e.g., various leukemias), carbonic anhydrase (associated with, e.g., renal cancer), aldolase A (associated with, e.g., lung cancer), PRAME (associated with, e.g., melanoma), HER-2/neu (associated with, e.g., breast, colon, lung and ovarian cancer), alpha-fetoprotein (associated with, e.g., hepatoma), KSA (associated with, e.g., colorectal cancer), gastrin (associated with, e.g., pancreatic and gastric cancer), telomerase catalytic protein, MUC-1 (associated with, e.g., breast and ovarian cancer), G-250 (associated with, e.g., renal cell carcinoma), p53 (associated with, e.g., breast, colon cancer), and carcinoembryonic antigen (associated with, e.g., breast cancer, lung cancer, and cancers of the gastrointestinal tract such as colorectal cancer), (d) shared antigens, for example, melanoma-melanocyte differentiation antigens such as MART-1/Melan A, gp100, MC1R, melanocyte-stimulating hormone receptor, tyrosinase, tyrosinase related protein-1/TRP1 and tyrosinase related protein-2/

TRP2 (associated with, e.g., melanoma), (e) prostate associated antigens such as PAP, PSA, PSMA, PSH-P1, PSM-P1, PSM-P2, associated with e.g., prostate cancer, (f) immunoglobulin idiotypes (associated with myeloma and B cell lymphomas, for example), and (g) other tumor antigens, such as polypeptide- and saccharide-containing antigens including (i) glycoproteins such as sialyl Tn and sialyl Le$^x$ (associated with, e.g., breast and colorectal cancer) as well as various mucins; glycoproteins may be coupled to a carrier protein (e.g., MUC-1 may be coupled to KLH); (ii) lipopolypeptides (e.g., MUC-1 linked to a lipid moiety); (iii) polysaccharides (e.g., Globo H synthetic hexasaccharide), which may be coupled to a carrier proteins (e.g., to KLH), (iv) gangliosides such as GM2, GM12, GD2, GD3 (associated with, e.g., brain, lung cancer, melanoma), which also may be coupled to carrier proteins (e.g., KLH).

Other tumor antigens include p15, Hom/Mel-40, H-Ras, E2A-PRL, H4-RET, IGH-IGK, MYL-RAR, Epstein Barr virus antigens, EBNA, human papillomavirus (HPV) antigens, including E6 and E7, hepatitis B and C virus antigens, human T-cell lymphotropic virus antigens, TSP-180, p185erbB2, p180erbB-3, c-met, mn-23H1, TAG-72-4, CA 19-9, CA 72-4, CAM 17.1, NuMa, K-ras, p16, TAGE, PSCA, CT7, 43-9F, 5T4, 791 Tgp72, beta-HCG, BCA225, BTAA, CA 125, CA 15-3 (CA 27.29\BCAA), CA 195, CA 242, CA-50, CAM43, CD68\KP1, CO-029, FGF-5, Ga733 (Ep-CAM), HTgp-175, M344, MA-50, MG7-Ag, MOV18, NB/70K, NY-CO-1, RCAS1, SDCCAG16, TA-90 (Mac-2 binding protein\cyclophilin C-associated protein), TAAL6, TAG72, TLP, TPS, and the like. These as well as other cellular components are described for example in United States Patent Publication No. 2002/0007173 and references cited therein.

Polynucleotide-containing antigens in accordance with the present invention typically comprise polynucleotides that encode polypeptide cancer antigens such as those listed above. Preferred polynucleotide-containing antigens include DNA or RNA vector constructs, such as plasmid vectors (e.g., pCMV), which are capable of expressing polypeptide cancer antigens in vivo.

Tumor antigens may be derived, for example, from mutated or altered cellular components. After alteration, the cellular components no longer perform their regulatory functions, and hence the cell may experience uncontrolled growth. Representative examples of altered cellular components include ras, p53, Rb, altered protein encoded by the Wilms' tumor gene, ubiquitin, mucin, protein encoded by the DCC, APC, and MCC genes, as well as receptors or receptor-like structures such as neu, thyroid hormone receptor, platelet derived growth factor (PDGF) receptor, insulin receptor, epidermal growth factor (EGF) receptor, and the colony stimulating factor (CSF) receptor. These as well as other cellular components are described for example in U.S. Pat. No. 5,693,522 and references cited therein.

Bacterial and viral antigens, may be used in conjunction with the compositions of the present invention for the treatment of cancer. In particular, carrier proteins, such as $CRM_{197}$, tetanus toxoid, or *Salmonella typhimurium* antigen may be used in conjunction/conjugation with compounds of the present invention for treatment of cancer. The cancer antigen combination therapies will show increased efficacy and bioavailability as compared with existing therapies.

Additional information on cancer or tumor antigens can be found, for example, in Moingeon (2001) *Vaccine* 19:1305-1326; Rosenberg (2001) *Nature* 411:380-384; Dermine et al. (2002) *Brit. Med. Bull.* 62:149-162; Espinoza-Delgado (2002) *The Oncologist* 7(suppl 3):20-33; Davis et al. (2003) *J. Leukocyte Biol.* 23:3-29; Van den Eynde et al. (1995) *Curr. Opin. Immunol.* 7:674-681; Rosenberg (1997) *Immunol. Today* 18:175-182; Offringa et al. (2000) *Curr. Opin. Immunol.* 2:576-582; Rosenberg (1999) *Immunity* 10:281-287; Sahin et al. (1997) *Curr. Opin. Immunol.* 9:709-716; Old et al. (1998) *J. Exp. Med.* 187:1163-1167; Chaux et al. (1999) *J. Exp. Med.* 189:767-778; Gold et al. (1965) *J. Exp. Med.* 122:467-468; Livingston et al. (1997) *Cancer Immunol. Immunother.* 45:1-6; Livingston et al. (1997) *Cancer Immunol. Immunother.* 45:10-19; Taylor-Papadimitriou (1997) *Immunol. Today* 18:105-107; Zhao et al. (1995) *J. Exp. Med.* 182:67-74; Theobald et al. (1995) *Proc. Natl. Acad. Sci. USA* 92:11993-11997; Gaudernack (1996) *Immunotechnology* 2:3-9; WO 91/02062; U.S. Pat. No. 6,015,567; WO 01/08636; WO 96/30514; U.S. Pat. No. 5,846,538; and U.S. Pat. No. 5,869,445.

Further antigens may also include an outer membrane vesicle (OMV) preparation.

Additional formulation methods and antigens (especially tumor antigens) are provided in U.S. Patent Publication No. 2004/0202680. See also U.S. Pat. No. 6,884,435.

J. Antigen References

The compositions of the invention can include antigens described in any of the following references:
1 International Publication No. WO99/24578.
2 International Publication No. WO99/36544.
3 International Publication No. WO99/57280.
4 International Publication No. WO00/22430.
5 Tettelin et al. (2000) *Science* 287:1809-1815.
6 International Publication No. WO96/29412.
7 Pizza et al. (2000) *Science* 287:1816-1820.
8 International Publication No. WO 01/52885.
9 Bjune et al. (1991) *Lancet* 338(8775):1093-1096.
10 Fuskasawa et al. (1999) *Vaccine* 17:2951-2958.
11 Rosenqist et al. (1998) *Dev. Biol. Strand* 92:323-333.
12 Constantino et al. (1992) *Vaccine* 10:691-698.
13 Constantino et al. (1999) *Vaccine* 17:1251-1263.
14 Watson (2000) *Pediatr. Infect. Dis. J.* 19:331-332.
15 Rubin (2000) *Pediatr. Clin. North Am.* 47:269-285.
16 Jedrzejas (2001) *Microbiol. Mol. Biol. Rev.* 65:187-207.
17 International Publication No. WO 02/02606.
18 Kalman et al. (1999) *Nature Genetics* 21:385-389.
19 Read et al. (2000) *Nucleic Acids Res.* 28:1397-1406.
20 Shirai et al. (2000) *J. Infect. Dis.* 181(Suppl 3):S524-S527.
21 International Publication No. WO99/27105.
22 International Publication No. WO00/27994.
23 International Publication No. WO00/37494.
24 International Publication No. WO99/28475.
25 Bell (2000) *Pediatr. Infect. Dis. J.* 19:1187-1188.
26 Iwarson (1995) *APMIS* 103:321-326.
27 Gerlich et al. (1990) *Vaccine* 8 Suppl:S63-S68, S79-S80.
28 Hsu et al. (1999) *Clin. Liver Dis.* 3:901-915.
29 Gastofsson et al. (1996) *N. Engl. J. Med.* 334:349-355.
30 Rappuoli et al. (1991) *TIBTECH* 9:232-238.
31 Plotkin, S. A. et al., *Vaccines*, 4$^{th}$ ed., W.B. Saunders Co. (2004)
32 Del Guidice et al. (1998) *Mol. Aspects. Med.* 19:1-70.
33 International Publication No. WO93/018150.
34 International Publication No. WO99/53310.
35 International Publication No. WO98/04702.
36 Ross et al. (2001) *Vaccine* 19:135-142.
37 Sutter et al. (2000) *Pediatr. Clin. North Am.* 47:287-308.
38 Zimmerman & Spann (1999) *Am. Fam. Physician* 59:113-118, 125-126.
39 Dreensen (1997) *Vaccine* 15 Suppl:S2-S6.

40 *MMWR Morb. Mortal Wkly Rep.* (1998) 16:47(1):12, 19.
41 McMichael (2000) *Vaccine* 19 Suppl 1:S101-S107.
42 Schuchat (1999) *Lancet* 353(9146):51-56.
43 GB patent applications 0026333.5, 0028727.6 & 0105640.7.
44 Dale (1999) *Infect. Disclin. North Am.* 13:227-243.
45 Ferretti et al. (2001) *Proc. Natl. Acad. Sci. USA* 98: 4658-4663.
46 Kuroda et al. (2001) *Lancet* 357(9264):1225-1240.
47 Ala'Aldeen et al. (2001) *Lancet* 357(9264):1218-1219.
48 Ramsay et al. (2001) *Lancet* 357(9251):195-196.
49 Lindberg (1999) *Vaccine* 17 Suppl 2:S28-S36.
50 Buttery & Moxon (2000) *J. R. Coil Physicians Long* 34:163-168.
51 Ahmad & Chapnick (1999) *Infect. Dis. Clin. North Am.* 13:113-133.
52 Goldblatt (1998) *J. Med. Microbiol.* 47:663-667.
53 European Patent No. EP 0 477 508B1.
54 U.S. Pat. No. 5,306,492.
55 International Publication No. WO98/42721.
56 Cruse et al. (eds.) *Conjugate Vaccines*, particularly vol. 10:48-114.
57 Hermanson, G. T., *Bioconjugate Techniques*, 1st ed., Academic Press (1996).
58 European Patent Publication No. 0 372 501.
59 European Patent Publication No. 0 378 881.
60 European Patent Publication No. 0 427 347.
61 International Publication No. WO 93/17712.
62 International Publication No. WO 98/58668.
63 European Patent Publication No. 0 471 177.
64 International Publication No. WO00/56360.
65 International Publication No. WO 00/67161.

The contents of all of the above cited patents, patent applications and journal articles are incorporated by reference as if set forth fully herein.

5. Optional Supplemental Components, Including Immunological Adjuvants

The immunogenic compositions of the present invention may include a wide variety of optional supplemental components.

Such supplemental components can be, for example, administered concurrently with the nanoparticle-containing compositions, e.g., in the same composition or in a separate composition. In another embodiment, supplemental components can be administered prior or subsequent to administration of the nanoparticle-containing compositions. When administered in the same composition, the supplemental components may be adsorbed on the surface of the nanoparticles, entrapped within the nanoparticles, dissolved or dispersed in solution while unbound to the nanoparticles, adsorbed to or entrapped within another group of nanoparticles, and so forth.

Such supplemental components include: (a) pharmaceuticals such as antibiotics and antiviral agents, nonsteroidal antiinflammatory drugs, analgesics, vasodilators, cardiovascular drugs, psychotropics, neuroleptics, antidepressants, antiparkinson drugs, beta blockers, calcium channel blockers, bradykinin inhibitors, ACE-inhibitors, vasodilators, prolactin inhibitors, steroids, hormone antagonists, antihistamines, serotonin antagonists, heparin, chemotherapeutic agents, antineoplastics and growth factors, including but not limited to PDGF, EGF, KGF, IGF-1 and IGF-2, FGF, (b) hormones including peptide hormones such as insulin, pro-insulin, growth hormone, GHRH, LHRH, EGF, somatostatin, SNX-111, BNP, insulinotropin, ANP, FSH, LH, PSH and hCG, gonadal steroid hormones (androgens, estrogens and progesterone), thyroid-stimulating hormone, inhibin, cholecystokinin, ACTH, CRF, dynorphins, endorphins, endothelin, fibronectin fragments, galanin, gastrin, insulinotropin, glucagon, GTP-binding protein fragments, guanylin, the leukokinins, magainin, mastoparans, dermaseptin, systemin, neuromedins, neurotensin, pancreastatin, pancreatic polypeptide, substance P, secretin, thymosin, and the like, (c) enzymes, (d) transcription or translation mediators, and (e) intermediates in metabolic pathways, and (f) immunomodulators, such as any of the various cytokines including interleukin-1, interleukin-2, interleukin-3, interleukin-4, and gamma-interferon.

In a preferred embodiment, the compositions of the invention include an immunological adjuvant. Adjuvants for use with the invention include, but are not limited to, one or more of the following set forth below:

A. Mineral Containing Compositions

Mineral containing compositions suitable for use as adjuvants include mineral salts, such as aluminum salts and calcium salts. The invention includes mineral salts such as hydroxides (e.g. oxyhydroxides), phosphates (e.g. hydroxyphosphates, orthophosphates), sulfates, etc. (see, e.g., *Vaccine Design: The Subunit and Adjuvant Approach* (Powell, M. F. and Newman, M. J. eds.) (New York: Plenum Press) 1995, Chapters 8 and 9), or mixtures of different mineral compounds (e.g. a mixture of a phosphate and a hydroxide adjuvant, optionally with an excess of the phosphate), with the compounds taking any suitable form (e.g. gel, crystalline, amorphous, etc.), and with adsorption to the salt(s) being preferred. The mineral containing compositions may also be formulated as a particle of metal salt (WO 00/23105).

Aluminum salts may be included in vaccines of the invention such that the dose of $Al^{3+}$ is between 0.2 and 1.0 mg per dose.

In one embodiment, the aluminum based adjuvant for use in the present invention is alum (aluminum potassium sulfate ($AlK(SO_4)_2$)), or an alum derivative, such as that formed in-situ by mixing an antigen in phosphate buffer with alum, followed by titration and precipitation with a base such as ammonium hydroxide or sodium hydroxide.

Another aluminum-based adjuvant for use in vaccine formulations of the present invention is aluminum hydroxide adjuvant ($Al(OH)_3$) or crystalline aluminum oxyhydroxide (AlOOH), which is an excellent adsorbant, having a surface area of approximately 500 $m^2/g$. In another embodiment, the aluminum based adjuvant is aluminum phosphate adjuvant ($AlPO_4$) or aluminum hydroxyphosphate, which contains phosphate groups in place of some or all of the hydroxyl groups of aluminum hydroxide adjuvant. Preferred aluminum phosphate adjuvants provided herein are amorphous and soluble in acidic, basic and neutral media.

In another embodiment, the adjuvant comprises both aluminum phosphate and aluminum hydroxide. In a more particular embodiment thereof, the adjuvant has a greater amount of aluminum phosphate than aluminum hydroxide, such as a ratio of 2:1, 3:1, 4:1, 5:1, 6:1, 7:1, 8:1, 9:1 or greater than 9:1, by weight aluminum phosphate to aluminum hydroxide. In another embodiment, aluminum salts in the vaccine are present at 0.4 to 1.0 mg per vaccine dose, or 0.4 to 0.8 mg per vaccine dose, or 0.5 to 0.7 mg per vaccine dose, or about 0.6 mg per vaccine dose.

Generally, the preferred aluminum-based adjuvant(s), or ratio of multiple aluminum-based adjuvants, such as aluminum phosphate to aluminum hydroxide is selected by optimization of electrostatic attraction between molecules such that the antigen carries an opposite charge as the adjuvant at the desired pH. For example, aluminum phosphate adjuvant (iep=4) adsorbs lysozyme, but not albumin at pH 7.4. Should albumin be the target, aluminum hydroxide adjuvant would be selected (iep 11.4). Alternatively, pretreatment of aluminum hydroxide with phosphate lowers its isoelectric point, making it a preferred adjuvant for more basic antigens.

B. Oil-emulsions

Oil-emulsion compositions and formulations suitable for use as adjuvants (with or without other specific immunostimulating agents such as muramyl peptides or bacterial cell wall components) include squalene-water emulsions, such as MF59 (5% Squalene, 0.5% Tween 80, and 0.5% Span 85, formulated into submicron particles using a microfluidizer). See WO 90/14837. See also, Podda (2001) *Vaccine* 19: 2673-2680; Frey et al. (2003) *Vaccine* 21:4234-4237. MF59 is used as the adjuvant in the FLUAD™ influenza virus trivalent subunit vaccine.

Particularly preferred adjuvants for use in the compositions are submicron oil-in-water emulsions. Preferred submicron oil-in-water emulsions for use herein are squalene/water emulsions optionally containing varying amounts of MTP-PE, such as a submicron oil-in-water emulsion containing 4-5% w/v squalene, 0.25-1.0% w/v Tween 80™ (polyoxyethylenesorbitan monooleate), and/or 0.25-1.0% Span 85™ (sorbitan trioleate), and, optionally, N-acetylmuramyl-L-alanyl-D-isogluatminyl-L-alanine-2-(1'-2'-dipalmitoyl-sn-glycero-3-huydroxyphosphosphoryloxy)-ethylamine (MTP-PE), for example, the submicron oil-in-water emulsion known as "MF59" (WO 90/14837; U.S. Pat. Nos. 6,299,884; 6,451,325; and Ott et al., "MF59—Design and Evaluation of a Safe and Potent Adjuvant for Human Vaccines" in *Vaccine Design: The Subunit and Adjuvant Approach* (Powell, M. F. and Newman, M. J. eds.) (New York: Plenum Press) 1995, pp. 277-296). MF59 contains 4-5% w/v Squalene (e.g. 4.3%), 0.25-0.5% w/v Tween 80™, and 0.5% w/v Span 85™ and optionally contains various amounts of MTP-PE, formulated into submicron particles using a microfluidizer such as Model 110Y microfluidizer (Microfluidics, Newton, Mass.). For example, MTP-PE may be present in an amount of about 0-500 µg/dose, more preferably 0-250 µg/dose and most preferably, 0-100 µg/dose. As used herein, the term "MF59-0" refers to the above submicron oil-in-water emulsion lacking MTP-PE, while the term MF59-MTP denotes a formulation that contains MTP-PE. For instance, "MF59-100" contains 100 µg MTP-PE per dose, and so on. MF69, another submicron oil-in-water emulsion for use herein, contains 4.3% w/v squalene, 0.25% w/v Tween 80™, and 0.75% w/v Span 85™ and optionally MTP-PE. Yet another submicron oil-in-water emulsion is MF75, also known as SAF, containing 10% squalene, 0.4% Tween 80™, 5% pluronic-blocked polymer L121, and thr-MDP, also microfluidized into a submicron emulsion. MF75-MTP denotes an MF75 formulation that includes MTP, such as from 100-400 µg MTP-PE per dose.

Submicron oil-in-water emulsions, methods of making the same and immunostimulating agents, such as muramyl peptides, for use in the compositions, are described in detail in WO 90/14837; U.S. Pat. Nos. 6,299,884; and 6,451,325.

Complete Freund's adjuvant (CFA) and incomplete Freund's adjuvant (IFA) may also be used as adjuvants in the invention.

C. Saponin Formulations

Saponin formulations are also suitable for use as adjuvants in the invention. Saponins are a heterologous group of sterol glycosides and triterpenoid glycosides that are found in the bark, leaves, stems, roots and even flowers of a wide range of plant species. Saponins isolated from the bark of the *Quillaia saponaria* Molina tree have been widely studied as adjuvants. Saponins can also be commercially obtained from *Smilax ornata* (sarsaprilla), *Gypsophilla paniculata* (brides veil), and *Saponaria officianalis* (soap root). Saponin adjuvant formulations include purified formulations, such as QS21, as well as lipid formulations, such as ISCOMs. Saponin adjuvant formulations include STIMULON® adjuvant (Antigenics, Inc., Lexington, Mass.).

Saponin compositions have been purified using High Performance Thin Layer Chromatography (HP-TLC) and Reversed Phase High Performance Liquid Chromatography (RP-HPLC). Specific purified fractions using these techniques have been identified, including QS7, QS17, QS18, QS21, QH-A, QH-B and QH-C. Preferably, the saponin is QS21. A method of production of QS21 is disclosed in U.S. Pat. No. 5,057,540. Saponin formulations may also comprise a sterol, such as cholesterol (see WO 96/33739).

Combinations of saponins and cholesterols can be used to form unique particles called Immunostimulating Complexes (ISCOMs). ISCOMs typically also include a phospholipid such as phosphatidylethanolamine or phosphatidylcholine. Any known saponin can be used in ISCOMs. Preferably, the ISCOM includes one or more of Quil A, QHA and QHC. ISCOMs are further described in EP 0 109 942, WO 96/11711 and WO 96/33739. Optionally, the ISCOMS may be devoid of (an) additional detergent(s). See WO 00/07621.

A review of the development of saponin based adjuvants can be found in Barr et al. (1998) *Adv. Drug Del. Rev.* 32:247-271. See also Sjolander et al. (1998) *Adv. Drug Del. Rev.* 32:321-338.

D. Virosomes and Virus Like Particles (VLPs)

Virosomes and Virus Like Particles (VLPs) are also suitable as adjuvants. These structures generally contain one or more proteins from a virus optionally combined or formulated with a phospholipid. They are generally non-pathogenic, non-replicating and generally do not contain any of the native viral genome. The viral proteins may be recombinantly produced or isolated from whole viruses. These viral proteins suitable for use in virosomes or VLPs include proteins derived from influenza virus (such as HA or NA), Hepatitis B virus (such as core or capsid proteins), Hepatitis E virus, measles virus, Sindbis virus, Rotavirus, Foot-and-Mouth Disease virus, Retrovirus, Norwalk virus, human Papilloma virus, HIV, RNA-phages, Qβ-phage (such as coat proteins), GA-phage, fr-phage, AP205 phage, and Ty (such as retrotransposon Ty protein p1). VLPs are discussed further in WO 03/024480; WO 03/024481; Niikura et al. (2002) *Virology* 293:273-280; Lenz et al. (2001) *J. Immunol.* 166(9): 5346-5355; Pinto et al. (2003) *J. Infect. Dis.* 188:327-338; and Gerber et al. (2001) *J. Virol.* 75(10):4752-4760. Virosomes are discussed further in, for example, Gluck et al. (2002) *Vaccine* 20:B10-B16. Immunopotentiating reconstituted influenza virosomes (IRIV) are used as the subunit antigen delivery system in the intranasal trivalent INFLEXAL™ product (Mischler and Metcalfe (2002) *Vaccine* 20 Suppl 5:B17-B23) and the INFLUVAC PLUS™ product.

E. Bacterial or Microbial Derivatives

Adjuvants suitable for use in the invention include bacterial or microbial derivatives such as:

(1) Non-toxic derivatives of enterobacterial lipopolysaccharide (LPS): Such derivatives include Monophosphoryl lipid A (MPL) and 3-O-deacylated MPL (3dMPL). 3dMPL is a mixture of 3 De-O-acylated monophosphoryl lipid A with 4, 5 or 6 acylated chains. A preferred "small particle" form of 3 De-O-acylated monophosphoryl lipid A is disclosed in EP 0 689 454. Such "small particles" of 3dMPL are small enough to be sterile filtered through a 0.22 micron membrane (see EP 0 689 454). Other non-toxic LPS derivatives include monophosphoryl lipid A mimics, such as aminoalkyl glucosaminide phosphate derivatives, e.g., RC-529. See Johnson et al. (1999) *Bioorg. Med. Chem. Lett.* 9:2273-2278.

(2) Lipid A Derivatives: Lipid A derivatives include derivatives of lipid A from *Escherichia coli* such as OM-174. OM-174 is described for example in Meraldi et al. (2003) *Vaccine* 21:2485-2491; and Pajak et al. (2003) *Vaccine* 21:836-842.

(3) Immunostimulatory oligonucleotides: Immunostimulatory oligonucleotides or polymeric molecules suitable for use as adjuvants in the invention include nucleotide sequences containing a CpG motif (a sequence containing an unmethylated cytosine followed by guanosine and linked by a phosphate bond). Bacterial double stranded RNA or oligonucleotides containing palindromic or poly(dG) sequences have also been shown to be immunostimulatory. The CpG's can include nucleotide modifications/analogs such as phosphorothioate modifications and can be double-stranded or single-stranded. Optionally, the guanosine may be replaced with an analog such as 2'-deoxy-7-deazaguanosine. See Kandimalla et al. (2003) *Nucl. Acids Res.* 31(9): 2393-2400; WO 02/26757; and WO 99/62923 for examples of possible analog substitutions. The adjuvant effect of CpG oligonucleotides is further discussed in Krieg (2003) *Nat. Med.* 9(7):831-835; McCluskie et al. (2002) *FEMS Immunol. Med. Microbiol.* 32:179-185; WO 98/40100; U.S. Pat. Nos. 6,207,646; 6,239,116; and 6,429,199.

The CpG sequence may be directed to TLR9, such as the motif GTCGTT or TTCGTT. See Kandimalla et al. (2003) *Biochem. Soc. Trans.* 31 (part 3):654-658. The CpG sequence may be specific for inducing a Th1 immune response, such as a CpG-A ODN, or it may be more specific for inducing a B cell response, such a CpG-B ODN. CpG-A and CpG-B ODNs are discussed in Blackwell et al. (2003) *J. Immunol.* 170(8): 4061-4068; Krieg (2002) *TRENDS Immunol.* 23(2): 64-65; and WO 01/95935. Preferably, the CpG is a CpG-A ODN.

Preferably, the CpG oligonucleotide is constructed so that the 5' end is accessible for receptor recognition. Optionally, two CpG oligonucleotide sequences may be attached at their 3' ends to form "immunomers". See, for example, Kandimalla et al. (2003) *BBRC* 306:948-953; Kandimalla et al. (2003) *Biochem. Soc. Trans.* 31(part 3):664-658; Bhagat et al. (2003) *BBRC* 300:853-861; and WO03/035836.

Immunostimulatory oligonucleotides and polymeric molecules also include alternative polymer backbone structures such as, but not limited to, polyvinyl backbones (Pitha et al. (1970) *Biochem. Biophys. Acta* 204(1):39-48; Pitha et al. (1970) *Biopolymers* 9(8):965-977), and morpholino backbones (U.S. Pat. Nos. 5,142,047; 5,185,444). A variety of other charged and uncharged polynucleotide analogs are known in the art. Numerous backbone modifications are known in the art, including, but not limited to, uncharged linkages (e.g., methyl phosphonates, phosphotriesters, phosphoamidates, and carbamates) and charged linkages (e.g., phosphorothioates and phosphorodithioates).

(4) ADP-ribosylating toxins and detoxified derivatives thereof: Bacterial ADP-ribosylating toxins and detoxified derivatives thereof may be used as adjuvants in the invention. Preferably, the protein is derived from *E. coli* (i.e., *E. coli* heat labile enterotoxin "LT"), cholera ("CT"), or pertussis ("PT"). The use of detoxified ADP-ribosylating toxins as mucosal adjuvants is described in WO 95/17211 and as parenteral adjuvants in WO 98/42375. Preferably, the adjuvant is a detoxified LT mutant such as LT-K63, LT-R72, and LTR192G. The use of ADP-ribosylating toxins and detoxified derivatives thereof, particularly LT-K63 and LT-R72, as adjuvants can be found in the following references: Beignon et al. (2002) *Infect. Immun.* 70(6):3012-3019; Pizza et al. (2001) *Vaccine* 19:2534-2541; Pizza et al. (2000) *Int. J. Med. Microbiol.* 290(4-5):455-461; Scharton-Kersten et al. (2000) *Infect. Immun.* 68(9):5306-5313; Ryan et al. (1999) *Infect. Immun.* 67(12):6270-6280; Partidos et al. (1999) *Immunol. Lett.* 67(3):209-216; Peppoloni et al. (2003) *Vaccines* 2(2):285-293; and Pine et al. (2002) *J. Control Release* 85(1-3):263-270. Numerical reference for amino acid substitutions is preferably based on the alignments of the A and B subunits of ADP-ribosylating toxins set forth in Domenighini et al. (1995) *Mol. Microbiol.* 15(6):1165-1167.

Compounds of formula I, II or III, or salts thereof, can also be used as adjuvants:

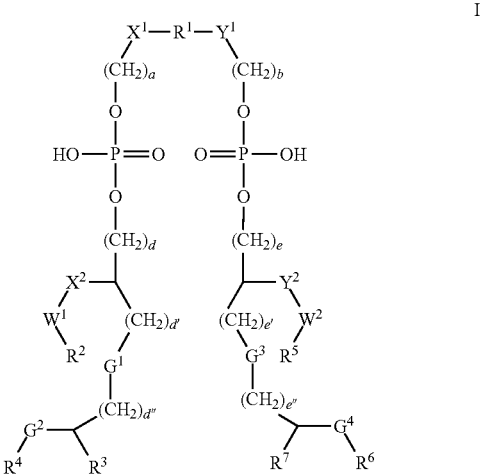

I

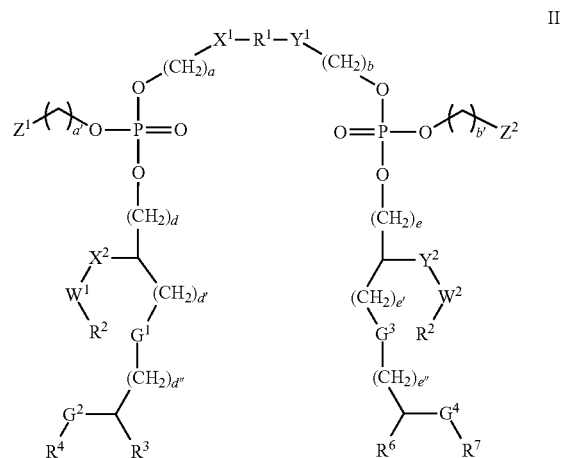

II

-continued

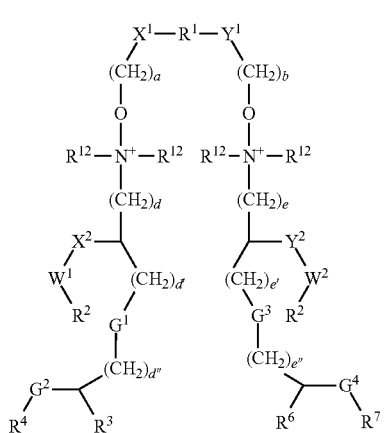

as defined in WO03/011223, such as 'ER 803058', 'ER 803732', 'ER 804053', ER 804058', 'ER 804059', 'ER 804442', 'ER 804680', 'ER 804764', ER 803022 or 'ER 804057' e.g.:

F. Human Immunomodulators

Human immunomodulators suitable for use as adjuvants include cytokines, such as interleukins (e.g. IL-1, IL-2, IL-4, IL-5, IL-6, IL-7, IL-12, etc.), interferons (e.g. interferon-γ), macrophage colony stimulating factor (M-CSF), and tumor necrosis factor (TNF).

G. Bioadhesives and Mucoadhesives

Bioadhesives and mucoadhesives may also be used as adjuvants. Suitable bioadhesives include esterified hyaluronic acid microspheres (Singh et al. (2001) *J. Cont. Release* 70:267-276) or mucoadhesives such as cross-linked derivatives of polyacrylic acid, polyvinyl alcohol, polyvinyl pyrollidone, polysaccharides and carboxymethylcellulose. Chitosan and derivatives thereof may also be used as adjuvants in the invention (see WO 99/27960).

H. Liposomes

Examples of liposome formulations suitable for use as adjuvants are described in U.S. Pat. Nos. 6,090,406; 5,916,588; and EP Patent Publication No. EP 0 626 169.

I. Polyoxyethylene Ether and Polyoxyethylene Ester Formulations

Adjuvants suitable for use in the invention include polyoxyethylene ethers and polyoxyethylene esters (see, e.g., WO

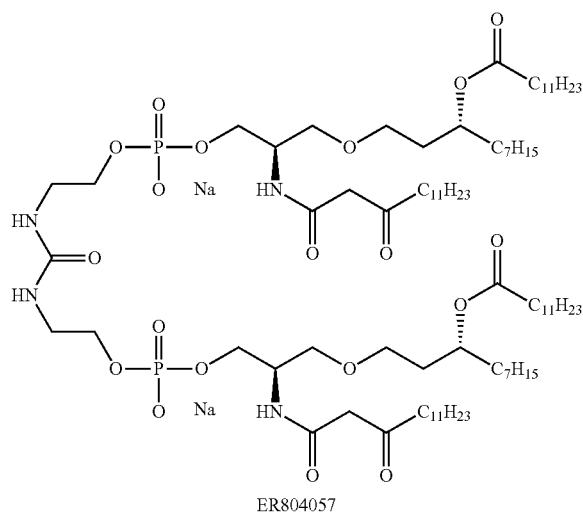

ER804057

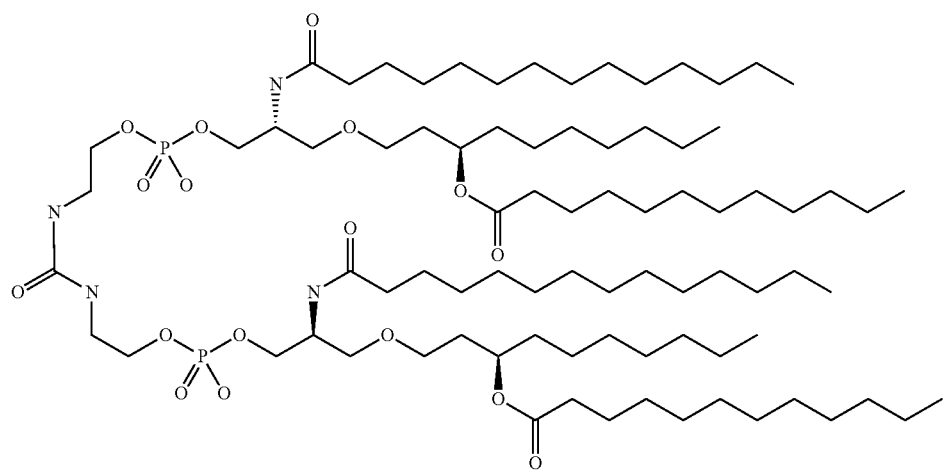

ER-803022

99/52549). Such formulations further include polyoxyethylene sorbitan ester surfactants in combination with an octoxynol (WO 01/21207) as well as polyoxyethylene alkyl ethers or ester surfactants in combination with at least one additional non-ionic surfactant such as an octoxynol (WO 01/21152).

Preferred polyoxyethylene ethers are selected from the following group: polyoxyethylene-9-lauryl ether (laureth 9), polyoxyethylene-9-steoryl ether, polyoxytheylene-8-steoryl ether, polyoxyethylene-4-lauryl ether, polyoxyethylene-35-lauryl ether, and polyoxyethylene-23-lauryl ether.

J. Polyphosphazene (PCPP)

PCPP formulations suitable for use as adjuvants are described, for example, in Andrianov et al. (1998) *Biomaterials* 19(1-3):109-115; and Payne et al. (1998) *Adv. Drug Del. Rev.* 31(3):185-196.

K. Muramyl Peptides

Examples of muramyl peptides suitable for use as adjuvants include N-acetyl-muramyl-L-threonyl-D-isoglutamine (thr-MDP), N-acetyl-normuramyl-1-alanyl-d-isoglutamine (nor-MDP), and N-acetylmuramyl-1-alanyl-d-isoglutaminyl-1-alanine-2-(1'-2'-dipalmitoyl-sn-glycero-3-hydroxyphosphoryloxy)-ethylamine MTP-PE).

L. Imidazoquinoline Compounds

Examples of imidazoquinoline compounds suitable for use as adjuvants include Imiquimod and its analogues, which are described further in Stanley (2002) *Clin. Exp. Dermatol.* 27(7):571-577; Jones (2003) *Curr. Opin. Investig. Drugs* 4(2):214-218; and U.S. Pat. Nos. 4,689,338; 5,389,640; 5,268,376; 4,929,624; 5,266,575; 5,352,784; 5,494,916; 5,482,936; 5,346,905; 5,395,937; 5,238,944; and 5,525,612.

M. Thiosemicarbazone Compounds

Examples of thiosemicarbazone compounds suitable for use as adjuvants, as well as methods of formulating, manufacturing, and screening for such compounds, include those described in WO 04/60308. The thiosemicarbazones are particularly effective in the stimulation of human peripheral blood mononuclear cells for the production of cytokines, such as TNF-α.

N. Tryptanthrin Compounds

Examples of tryptanthrin compounds suitable for use as adjuvants, as well as methods of formulating, manufacturing, and screening for such compounds, include those described in WO 04/64759. The tryptanthrin compounds are particularly effective in the stimulation of human peripheral blood mononuclear cells for the production of cytokines, such as TNF-α.

O. Nucleoside Analogs

Various nucleoside analogs can be used as adjuvants, such as (a) Isatorabine (ANA-245; 7-thia-8-oxoguanosine):

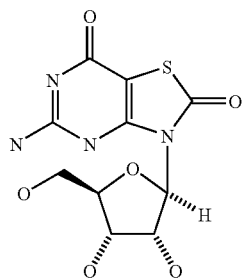

an U d prodrugs thereof; (b) ANA975; (c) ANA-025-1; (d) ANA380; (e) the compounds disclosed in U.S. Pat. No. 6,924,271; U.S. Publication No. 2005/0070556; and U.S. Pat. No. 5,658,731; (f) a compound having the formula:

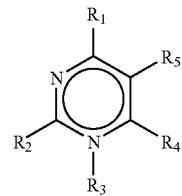

wherein:
$R_1$ and $R_2$ are each independently H, halo, —$NR_aR_b$, —OH, $C_{1-6}$ alkoxy, substituted $C_{1-6}$ alkoxy, heterocyclyl, substituted heterocyclyl, $C_{6-10}$ aryl, substituted $C_{6-10}$ aryl, $C_{1-6}$ alkyl, or substituted $C_{1-6}$ alkyl;

$R_3$ is absent, H, $C_{1-6}$ alkyl, substituted $C_{1-6}$ alkyl, $C_{6-10}$ aryl, substituted $C_{6-10}$ aryl, heterocyclyl, or substituted heterocyclyl;

$R_4$ and $R_5$ are each independently H, halo, heterocyclyl, substituted heterocyclyl, —C(O)—$R_d$, $C_{1-6}$ alkyl, substituted $C_{1-6}$ alkyl, or bound together to form a 5 membered ring as in $R_{4-5}$:

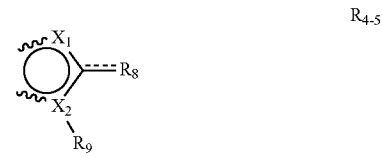

the binding being achieved at the bonds indicated by a ∿∿∿

$X_1$ and $X_2$ are each independently N, C, O, or S;

$R_8$ is H, halo, —OH, $C_{1-6}$ alkyl, $C_{2-6}$ alkenyl, $C_{2-6}$ alkynyl, —OH, —$NR_aR_b$, —$(CH_2)_n$—O—$R_c$, —O—$(C_{1-6}$ alkyl), —$S(O)_pR_e$, or —C(O)—$R_d$;

$R_9$ is H, $C_{1-6}$ alkyl, substituted $C_{1-6}$ alkyl, heterocyclyl, substituted heterocyclyl or $R_{9a}$, wherein $R_{9a}$ is:

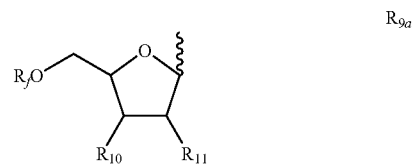

the binding being achieved at the bond indicated by a ∿∿∿

$R_{10}$ and $R_{11}$ are each independently H, halo, $C_{1-6}$ alkoxy, substituted $C_{1-6}$ alkoxy, —$NR_aR_b$, or —OH;

each $R_a$ and $R_b$ is independently H, $C_{1-6}$ alkyl, substituted $C_{1-6}$ alkyl, —C(O)$R_d$, $C_{6-10}$ aryl;

each $R_c$ is independently H, phosphate, diphosphate, triphosphate, $C_{1-6}$ alkyl, or substituted $C_{1-6}$ alkyl;

each $R_d$ is independently H, halo, $C_{1-6}$ alkyl, substituted $C_{1-6}$ alkyl, $C_{1-6}$ alkoxy, substituted $C_{1-6}$ alkoxy, —$NH_2$, —$NH(C_{1-6}$ alkyl), —NH(substituted $C_{1-6}$ alkyl), —$N(C_{1-6}$ alkyl$)_2$, —N(substituted $C_{1-6}$ alkyl$)_2$, $C_{6-10}$ aryl, or heterocyclyl;

each $R_e$ is independently H, $C_{1-6}$ alkyl, substituted $C_{1-6}$ alkyl, $C_{6-10}$ aryl, substituted $C_{6-10}$ aryl, heterocyclyl, or substituted heterocyclyl;

each $R_f$ is independently H, $C_{1-6}$ alkyl, substituted $C_{1-6}$ alkyl, —C(O)$R_d$, phosphate, diphosphate, or triphosphate;

each n is independently 0, 1, 2, or 3;
each p is independently 0, 1, or 2; or
or (g) a pharmaceutically acceptable salt of any of (a) to (f), a tautomer of any of (a) to (f), or a pharmaceutically acceptable salt of the tautomer.

P. Lipids Linked to a Phosphate-containing Acyclic Backbone

Adjuvants containing lipids linked to a phosphate-containing acyclic backbone include the TLR4 antagonist E5564 (Wong et al. (2003) *J. Clin. Pharmacol.* 43(7):735-742; US2005/0215517):

Q. Small Molecule Immunopotentiators (SMIPS)
SMIPs include:
N2-methyl-1-(2-methylpropyl)-1H-imidazo[4,5-c]quinoline-2,4-diamine;
N2,N2-dimethyl-1-(2-methylpropyl)-1H-imidazo[4,5-c]quinoline-2,4-diamine;
N2-ethyl-N2-methyl-1-(2-methylpropyl)-1H-imidazo[4,5-c]quinoline-2,4-diamine;
N2-methyl-1-(2-methylpropyl)-N2-propyl-1H-imidazo[4,5-c]quinoline-2,4-diamine;
1-(2-methylpropyl)-N2-propyl-1H-imidazo[4,5-c]quinoline-2,4-diamine;
N2-butyl-1-(2-methylpropyl)-1H-imidazo[4,5-c]quinoline-2,4-diamine;
N2-butyl-N2-methyl-1-(2-methylpropyl)-1H-imidazo[4,5-c]quinoline-2,4-diamine;
N2-methyl-1-(2-methylpropyl)-N2-pentyl-1H-imidazo[4,5-c]quinoline-2,4-diamine;
N2-methyl-1-(2-methylpropyl)-N2-prop-2-enyl-1H-imidazo[4,5-c]quinoline-2,4-diamine;
1-(2-methylpropyl)-2-[(phenylmethyl)thio]-1H-imidazo[4,5-c]quinolin-4-amine;
1-(2-methylpropyl)-2-(propylthio)-1H-imidazo[4,5-c]quinolin-4-amine;
2-[[4-amino-1-(2-methylpropyl)-1H-imidazo[4,5-c]quinolin-2-yl]methyl)amino]ethanol;
2-[[4-amino-1-(2-methylpropyl)-1H-imidazo[4,5-c]quinolin-2-yl](methyl)amino]ethyl acetate;
4-amino-1-(2-methylpropyl)-1,3-dihydro-2H-imidazo[4,5-c]quinolin-2-one;
N2-butyl-1-(2-methylpropyl)-N4,N4-bis(phenylmethyl)-1H-imidazo[4,5-c]quinoline-2,4-diamine;
N2-butyl-N2-methyl-1-(2-methylpropyl)-N4,N4-bis(phenylmethyl)-1H-imidazo[4,5-c]quinoline-2,4-diamine;
N2-methyl-1-(2-methylpropyl)-N4,N4-bis(phenylmethyl)-1H-imidazo[4,5-c]quinoline-2,4-diamine;
N2,N2-dimethyl-1-(2-methylpropyl)-N4,N4-bis(phenylmethyl)-1H-imidazo[4,5-c]quinoline-2,4-diamine;
1-{4-amino-2-[methyl(propyl)amino]-1H-imidazo[4,5-c]quinolin-1-yl}-2-methylpropan-2-ol;
1-[4-amino-2-(propylamino)-1H-imidazo[4,5-c]quinolin-1-yl]-2-methylpropan-2-ol;
N4,N4-dibenzyl-1-(2-methoxy-2-methylpropyl)-N2-propyl-1H-imidazo[4,5-c]quinoline-2,4-diamine.

R. Proteosomes

One adjuvant is an outer membrane protein proteosome preparation prepared from a first Gram-negative bacterium in combination with a liposaccharide preparation derived from a second Gram-negative bacterium, wherein the outer membrane protein proteosome and liposaccharide preparations form a stable non-covalent adjuvant complex. Such complexes include "IVX-908", a complex comprised of *Neisseria meningitidis* outer membrane and lipopolysaccharides. They have been used as adjuvants for influenza vaccines (WO02/072012).

S. Other Adjuvants

Other substances that act as immunostimulating agents are disclosed in Burdman, J. R. et al. (eds) (1995) (*Vaccine Design: Subunit and Adjuvant Approach* (Springer) (Chapter 7) and O'Hagan, D. T. (2000) (*Vaccine Adjuvants: Preparation Methods and Research Protocols* (Humana Press) (Volume 42 of *Methods in Molecular Medicine* series)).

Further useful adjuvant substances include:
Methyl inosine 5'-monophosphate ("MIMP") (Signorelli & Hadden (2003) *Int. Immunopharmacol.* 3(8):1177-1186).

A polyhydroxlated pyrrolizidine compound (WO2004/064715), such as one having formula:

where R is selected from the group comprising hydrogen, straight or branched, unsubstituted or substituted, saturated or unsaturated acyl, alkyl (e.g. cycloalkyl), alkenyl, alkynyl and aryl groups, or a pharmaceutically acceptable salt or derivative thereof. Examples include, but are not limited to: casuarine, casuarine-6-α-D-glucopyranose, 3-epi-casuarine, 7-epi-casuarine, 3,7-diepi-casuarine, etc.

A gamma inulin (Cooper (1995) *Pharm. Biotechnol.* 6:559-580) or derivative thereof, such as algammulin.

Compounds disclosed in PCT/US2005/022769.

Compounds disclosed in WO2004/87153, including: Acylpiperazine compounds, Indoledione compounds, Tetrahydraisoquinoline (THIQ) compounds, Benzocyclodione compounds, Aminoazavinyl compounds, Aminobenzimidazole quinolinone (ABIQ) compounds (U.S. Pat. No. 6,605,617; WO 02/18383), Hydrapthalamide compounds, Benzophenone compounds, Isoxazole compounds, Sterol compounds, Quinazilinone compounds, Pyrrole compounds (WO2004/018455), Anthraquinone compounds, Quinoxaline compounds, Triazine compounds, Pyrazalopyrimidine compounds, and Benzazole compounds (WO03/082272).

Loxoribine (7-allyl-8-oxoguanosine) (U.S. Pat. No. 5,011,828).

A formulation of a cationic lipid and a (usually neutral) co-lipid, such as aminopropyl-dimethyl-myristoleyloxy-propanaminium bromide-diphytanoylphosphatidyl-ethanolamine ("Vaxfectin™") or aminopropyl-dimethyl-bis-dodecyloxy-propanaminium bromide-dioleoylphosphatidyl-ethanolamine ("GAP-DLRIE: DOPE"). Formulations containing (±)-N-(3-aminopropyl)-N,N-dimethyl-2,3-bis(syn-9-tetradeceneyloxy)-1-propanaminium salts are preferred (U.S. Pat. No. 6,586,409).

The invention may also comprise combinations of aspects of one or more of the adjuvants identified above. For example, the following adjuvant compositions may be used in the invention: (1) a saponin and an oil-in-water emulsion (WO 99/11241); (2) a saponin (e.g., QS21)+a non-toxic LPS derivative (e.g. 3dMPL) (see WO 94/00153); (3) a saponin (e.g., QS21)+a non-toxic LPS derivative (e.g. 3dMPL)+a cholesterol; (4) a saponin (e.g., QS21)+3dMPL+IL-12 (optionally+a sterol) (WO 98/57659); (5) combinations of 3dMPL with, for example, QS21 and/or oil-in-water emulsions (see EP 0 835 318; EP 0 735 898; and EP 0 761 231); (6) SAF, containing 10% Squalane, 0.4% Tween 80, 5% pluronic-block polymer L121, and thr-MDP, either microfluidized into a submicron emulsion or vortexed to generate a larger particle size emulsion; (7) Ribi™ adjuvant system (RAS), (Ribi Immunochem, Hamilton, Mont.) containing 2% Squalene, 0.2% Tween 80, and one or more bacterial cell wall components from the group consisting of monophosphorylipid A (MPL), trehalose dimycolate (TDM), and cell wall skeleton (CWS), preferably MPL+CWS (Detox™); (8) one or more mineral salts (such as an aluminum salt)+a non-toxic derivative of LPS (such as 3dPML); (9) one or more mineral salts (such as an aluminum salt)+an immunostimulatory oligonucleotide (such as a nucleotide sequence including a CpG motif).

Aluminum salts and MF59 are preferred adjuvants for use with injectable influenza vaccines. Bacterial toxins and bioadhesives are preferred adjuvants for use with mucosally-delivered vaccines, such as nasal vaccines.

6. Administration

Once formulated (and resuspended, if necessary), the nanoparticle compositions of the invention can be administered parenterally, e.g., by injection (which may be needleless). In this regard, the nanoparticle compositions may be supplied lyophilized in a vial or other container which is supplied with a septum or other suitable means for supplying a resuspension medium (e.g., Water for Injection) and for withdrawing the resultant suspension. A suitable syringe may also be supplied for injection.

The compositions can be injected subcutaneously, intradermally, intramuscularly, intravenously, intraarterially, or intraperitoneally, for example. Other modes of administration include nasal, mucosal, intraoccular, rectal, vaginal, oral and pulmonary administration, and transdermal or transcutaneous applications.

In some embodiments, the compositions of the present invention can be used for site-specific targeted delivery. For example, intravenous administration of the compositions can be used for targeting the lung, liver, spleen, blood circulation, or bone marrow.

The nanoparticle compositions of the present invention will generally include one or more pharmaceutically acceptable excipients. For example, vehicles such as water, saline, glycerol, polyethylene glycol, hyaluronic acid, ethanol, etc. may be used. Other excipients, such as wetting or emulsifying agents, biological buffering substances, and the like, may be present. A biological buffer can be virtually any solution which is pharmacologically acceptable and which provides the formulation with the desired pH, i.e., a pH in the physiological range. Examples include saline, phosphate buffered saline, Tris buffered saline, Hank's buffered saline, and the like. Depending on the final dosage form, other excipients known in the art can also be introduced, including binders, disintegrants, fillers (diluents), lubricants, glidants (flow enhancers), compression aids, colors, sweeteners, preservatives, suspending/dispersing agents, film formers/coatings, flavors and printing inks.

Treatment may be conducted according to a single dose schedule or a multiple dose schedule. A multiple dose schedule is one in which a primary course of administration may be given, for example, with 1-10 separate doses, followed by other doses given at subsequent time intervals, chosen to maintain and/or reinforce the therapeutic response, for example at 1-4 months for a second dose, and if needed, a subsequent dose(s) after several months. The dosage regimen will also be, at least in part, determined by the need of the subject and be dependent on the judgment of the practitioner.

Furthermore, if prevention of disease is desired, the compositions are generally administered prior to the arrival of the primary occurrence of the infection or disorder of interest. If other forms of treatment are desired, e.g., the reduction or elimination of symptoms or recurrences, the compositions are generally administered subsequent to the arrival of the primary occurrence of the infection or disorder of interest.

7. Kits

This invention encompasses kits which can simplify the administration of appropriate amounts of active ingredients to a subject. A typical kit of the invention comprises a unit dosage form of a lyophilized nanoparticle composition of the invention, preferably in a sealed container. Kits of the invention can further comprise pharmaceutically acceptable vehicles that can be used to administer one or more active ingredients. Thus, in a particular embodiment, the kit further comprises a sealed container of a suitable vehicle in which the nanoparticle composition can be dissolved to form a particulate-free sterile solution that is suitable for administration, and a device that can be used to administer the active ingredient. Examples of such devices include, but are not limited to, syringes, drip bags, patches, and inhalers.

C. Experimental

Below are examples of specific embodiments for carrying out the present invention. The examples are offered for illustrative purposes only, and are not intended to limit the scope of the present invention in any way.

Efforts have been made to ensure accuracy with respect to numbers used (e.g., amounts, temperatures, etc.), but some experimental error and deviation should, of course, be allowed for.

The sucrose, mannitol, glucose, trehalose, dextran (MW=70,000), Bovine Serum Albumin (BSA), and ovalbumin, chicken egg white (ovalbumin or OVA), polyvinylpyrrolidone (MW=40,000), carboxymethylcellulose (MW=90,000), Pluronic F68 (also known as poloxamer 188) and all other chemicals were from Sigma Chemicals (St. Louis, Mo.). Polyvinyl alcohol (MW=15,000) was from ICN Biomedicals (now MP Biomedicals, Irvine, Calif.). Acetone was from EMD Chemicals (Gibbstown, N.J.).

Influenza antigens (FluCC) and *Neisseria meningitidis* serotype B antigen (Men B 287) were from Chiron Vaccines. *Escherichia coli*-derived recombinant *Neisseria meningitidis* serotype B vaccine candidate, Men B 287 (Chiron Vaccines, IRIS, Chiron, S.r.l., Siena, Italy) was isolated and purified as described previously (M. Comanducci, et al. (2002) *J. Exp. Med.* 195: 1445-1454). GBS1 was from Chiron Vaccines and was identified and purified as previously described (D. Maione et al. (2005) *Science* 309: 148-150).

EXAMPLE 1

Nanoparticle and Microparticle Preparation

With the nanoprecipitation method (see Fessi, H., F. Puisieux, and J. P. Devissaguet, "Process for the preparation of dispersible colloidal systems of a substance in the form of nanocapsules," European Patent No. 0274961B1, corresponding to Devissaguet et al. U.S. Pat. No. 5,049,322), particles ranging in size from 100 nm to 500 nm were created. Specifically, ~100 to ~120 nm particles were created by dissolving RG503, a PLG polymer having a 50:50 lactide/glycolide molar ratio and a molecular weight of ~30 kDaltons, available from Boehringer Ingelheim, in acetone (0.5% wt/vol) and adding this solution dropwise to an equal volume of water with magnetic stirring at 600 rpm and allowing the acetone to evaporate. RG 752, a PLG having a 75:25 lactide/glycolide molar ratio and a molecular weight of ~20 kDaltons, available from Boehringer Ingelheim, was also employed in one instance.

The different size nanoparticles were created by adjusting the initial PLG concentration in the organic phase or by switching the solvent from acetone to THF. Increasing the PLG concentration increased the particle size, while switching from acetone to THF also increased particle size. There have been several literature reports that discussed the parameters that allowed for the preparation of various size nanoparticles (P. D. Scholes et al. (1993) *J. Control Release* 25:145-153; L. Peltonen et al. (2002) *AAPS PharmSciTech* 3: E32; P. Wehrle et al. (1995) *Eur. J. Pharmaceut. Biopharmaceut.* 41:19-26). For example, small particles (~120 nm) were prepared with 25 mL of 0.5% (w/v) PLG in acetone added to 25 mL water. Intermediate sized particles (~180 nm) were made with 25 mL of 0.5% (w/v) PLG in tetrahydrofuran (THF) added to 25 mL water. Large particles (~230 nm) were prepared with 12.5 mL 4% (w/v) PLG in acetone added to 40 mL water.

Microparticles with 0.05% dioctyl sodium sulfosuccinate (DSS), of size ~1 µm, were prepared by a previously established double emulsion, solvent evaporation method (see Singh, M., et al. (2004) *J. Pharm. Sci.*, 93(2): 273-282), which differs significantly from the nanoparticle preparation method. Specifically, a water/oil/water emulsion technique was used to form the microparticles. The PLG was dissolved in dichloromethane (DCM) (6% wt./vol.) and added to a phosphate buffered saline aqueous phase (1:4 water:oil) (v:v) and homogenized for 2 minutes. This water-in-oil emulsion was then added to water containing DSS (1:4 water-in-oil emulsion: water) (v:v) and homogenized on an ice bath at high speed for 10 minutes. The resulting suspension was magnetically stirred to allow the DCM to evaporate. The microparticles had an average size (D(volume, 50%) of 0.83 µm and a ((D(volume, 90%) of 1.24 µm.

One advantage for nanoparticles compared to microparticles was the ease of preparation. The nanoparticle method was based on a single phase and did not need high shear homogenization, only magnetic stirring. The type of organic solvent used with the two methods was different. The nanoparticle method used acetone, compared to the more toxic DCM used in the microparticle method. The Food and Drug Administration (FDA) classifies DCM as a Class 2 solvent and limits its use in pharmaceutical products. Acetone is a Class 3 solvent and the FDA has higher limits on the amount of allowable residual solvent.

EXAMPLE 2

Sterile Filtration of Nanoparticles

As previously indicated, one advantage of the smaller nanoparticles is that they can be sterile filtered after particle preparation. In this Example, nanoparticles were prepared in the range of 110 to 230 nm and sterile filtered with a Pall Acrodisc 0.2 µm filter. Nanoparticle size was measured with a Zetasizer 3000HSA (Malvern Instruments, UK) for sub-500 nm particles. Larger particles and aggregates were measured with a Horiba LA-930 (Irvine, Calif., USA). This instrument is based on static light scattering to determine particle size, while the Zetasizer used dynamic light scattering to detect the smaller particles.

The zeta potential was measured with the Zetasizer with a typical diluted concentration of 0.2 mg/mL PLG in a specified diluent. For the 120 nm nanoparticles, the zeta potential in 10 mM Sodium Citrate was −39 mV and in 10 mM Sodium Phosphate, pH=7.0, it was −48 mV. The zeta potential was in the range expected for the anionic PLG.

PLG concentration was measured pre- and post-sterile filtration by placing 1 mL of each sample, which was lyophilized, in a pre-weighed vial, and the PLG content was determined by the mass remaining. In general, only the smaller nanoparticles (~120 nm) had PLG concentrations comparable to pre-sterile filtration values, with substantially no change in particle size being observed. See Table 1. Endotoxin levels (LAL) of the sterile filtered nanoparticles were in the range 0.48-0.96 EU/mL. As can be seen, only the small microparticles (~120 nm) had PLG concentrations comparable to pre-sterile filtration values, with no change in particle size. The size of the sterile filtered 181 nm particles was not determined.

TABLE 1

| | Pre Sterile Filtration | | Post Sterile Filtration | |
|---|---|---|---|---|
| PLG | Size (nm) | PLG content (mg/ml) | Size (nm) | PLG content (mg/ml) |
| RG503 | 124.3 | 5.3 | 119.9 | 4.9 |
| RG503 | 118.0 | 6.0 | 116.1 | 5.3 |
| RG503 | 181.4 | 5.3 | — | 0.5 |
| RG752 | 158.6 | 4.9 | 148.3 | 2.6 |
| RG503 | 122.4 | 5.9 | 119.7 | 5.4 |

EXAMPLE 3

Resuspension of Nanoparticles Post-Lyophilization

One disadvantage of nanoparticles relative to microparticles is that, post-lyophilization, they do not necessarily resuspend to the size that they were pre-lyophilization. In the present example, surfactants and/or cryoprotective agents were pipetted into the nanoparticle suspensions immediately prior to lyophilization. The suspensions were placed in glass vials and frozen at −80° C. for 30 minutes. Lyophilization was carried out in a Labconco Freeze Dry System, Freezone 4.5 (Kansas City, Mo., USA) operating at −49° C. and vacuum less than $133 \times 10^{-3}$ mBar. After lyophilization, 5-10 mg of nanoparticles were resuspended in 1 ml of water and sized. Prior to nanoparticle size measurement, the sample was diluted 50 μL, in 2 mL.

As seen from Table 2 below, excipients can be added which allow lyophilized nanoparticles to be resuspended, without an unacceptable increase in size (e.g., without significant aggregation). For example, a surfactant can be used to resuspend the nanoparticles (e.g., PVA, 131% w/w (wt PVA/wt PLG)). Moreover, the amount of surfactant can be reduced by using combinations of surfactants and cryoprotective agents. Examples of such formulations include 10% (wt/wt) PVA with 3% (wt/vol) sucrose and 4% (wt/vol) mannitol, 10% (wt/wt) PVA with 5% (wt/vol) trehalose and 2.5% (wt/vol) mannitol, and 0.5% (wt/wt) DSS with 5% (wt/vol) trehalose and 2.5% (wt/vol) mannitol.

philized vaccine formulation. With protein antigens, it has been shown that sucrose and trehalose help to stabilize the proteins during the lyophilization process (J. F. Carpenter et al. (1997) *Pharm. Res.* 14: 969-975). Mannitol is a bulking agent that is used as scaffolding to avoid collapse of the cake during the freeze-drying process (X. Tang and M. J. Pikal (2004) *Pharm. Res.* 21: 191-200). With the addition of appropriate sugars, e.g., sucrose and mannitol or trehalose and mannitol, the amount of PVA needed was reduced to 10% (wt./wt.). With a typical formulation containing 10 to 20 mg/mL PLG this is equivalent to 1-2 mg/mL PVA. With 10% (wt/wt) CMC, PVP, or Pluronic F68 and sucrose and mannitol, the particles were aggregated. The combination and concentration of sugars satisfy the isotonicity requirement, form an elegant cake post lyophilization, and serve to stabilize the protein antigen. The osmolarity of a vaccine product should be in the range of 280 to 330 mOsm/L. The concentrations of sucrose and mannitol or trehalose and mannitol used with the PVA are in the appropriate osmolarity range and lead to a lyophilized cake that is the same size as the initial liquid volume. DSS was also found to provide adequate resuspension at sufficient concentration in trehalose and mannitol.

Large (221 nm) and small (122 nm) nanoparticles were also analyzed upon resuspension using varying concentrations of PVA (wt/wt PLG) plus 4% sucrose (w/v) and 3% mannitol (w/v). The PLG content was 5 mg/mL. The amount of polyvinyl alcohol (PVA) associated with the pellet versus free in solution was measured by first separating the solid phase of the suspension by centrifugation (Eppendorf 5415D,

TABLE 2

| Excipient | Initial Size (nm) | Post-lyophilization Size (nm) | Behavior |
|---|---|---|---|
| None | 125 | 113461 | aggregated |
| 10%(w/v) sucrose | 127 | 25666 | aggregated |
| 4% (w/v) sucrose + 3% (w/v) mannitol | 125 | 64659 | aggregated |
| 0.5% DSS (w/w) | ~120 | 102000 | aggregated |
| 5% DSS (w/w) | ~120 | 127,000 | aggregated |
| 0.5% DSS (w/w)/4% sucrose + 3% mannitol (w/v) | 112 | 25237 | aggregated |
| 0.05% DSS (w/w)/5% trehalose + 2.5% mannitol (w/v) | ~120 | 37000 | aggregated |
| 0.1% DSS (w/w)/5% trehalose + 2.5% mannitol (w/v) | ~120 | 18000 | aggregated |
| 0.25% DSS (w/w)/5% trehalose + 2.5% mannitol (w/v) | ~120 | 22000 | aggregated |
| 10% (w/v) mannitol | 127 | 26100 | aggregated |
| 10% (w/v) dextran | 127 | 21359 | aggregated |
| 5% glucose (w/v) | ~120 | 28000 | aggregated |
| 5% trehalose + 2.5% mannitol (w/v) | ~120 | 55000 | aggregated |
| 100% (w/w) Pluronic F-68 | ~120 | 64000 | aggregated |
| 131% (w/w) Pluronic F-68 | ~120 | 74000 | aggregated |
| 10% (w/w) Pluronic F-68/4% sucrose + 3% mannitol (w/v) | ~120 | 61000 | aggregated |
| 66% (w/w) CMC | 127 | 26572 | aggregated |
| 131% (w/w) CMC | ~120 | 14000 | aggregated |
| 10% (w/w) CMC/4% sucrose + 3% mannitol (w/v) | ~120 | 25000 | aggregated |
| 66% (w/w) PVP | 127 | 25758 | aggregated |
| 100% (w/w) PVP | ~120 | 133 | resuspended |
| 131% (w/w) PVP | ~120 | 137 | resuspended |
| 10% (w/w) PVP/4% sucrose + 3% mannitol (w/v) | ~120 | 30000 | aggregated |
| 10% (w/w) PVA | 127 | 18507 | aggregated |
| 66% (w/w) PVA | 127 | 441 | aggregated |
| 100% (w/w) PVA | ~120 | 148 | resuspended |
| 131% (w/w) PVA (5 mg/mL PVA) | 127 | 155 | resuspended |
| 10% (w/w) PVA/4% sucrose + 3% mannitol (w/v) | 121 | 146 | resuspended |
| 0.5% (w/w) DSS/5% trehalose + 2.5% mannitol (w/v) | 112 | 143 | resuspended |
| 10% PVA (w/w)/5% trehalose + 2.5% mannitol (w/v) | 122 | 140 | resuspended |

More particularly, sugars alone resulted in nanoparticle aggregation. Surfactant alone (i.e., PVA) allowed for nanoparticle resuspension. Improved resuspension results were achieved with formulations containing sugars and surfactant. Sugars additionally serve two important functions for a lyo- 20 minutes at 13200 rpm) and removing the supernatant fraction. Both mixtures were hydrolyzed overnight in 2N NaOH, pH neutralized and an aliquot of the clear solution was analyzed following a previously described method (J. H. Finley (1961) *Anal. Chem.* 33: 1925-1927); E. Allemann et al.

(1998) *Adv. Drug Delivery Rev.* 34: 171-189), in which 0.2 mL of the test solution was mixed with 1.00 mL of 4% w/w boric acid and 0.20 mL of an iodine solution (1.27% w/w $I_2$ and 2.5% w/w KI) and the absorbance read at 644 nm and compared to a calibration curve with linearity >0.995 ($R^2$).

Results are presented in Table. 3. Without wishing to be bound by theory, it is believed that additional PVA needed to resuspend the smaller nanoparticles is most likely due primarily to their larger surface area compared to the larger nanoparticles, although there was also likely an effect to due partitioning of the PVA between the surface and the solution.

TABLE 3

| PVA concentration | total PVA (µg PVA/mg PLG) | final size | pellet (µg PVA/mg PLG) |
|---|---|---|---|
| Small Nanoparticles (122 nm) | | | |
| 1%(w/w) PVA | 10 | 47 µm | 8 |
| 3%(w/w) PVA | 30 | 24 µm | 13 |
| 5%(w/w) PVA | 50 | 15 µm | 18 |
| 7%(w/w) PVA | 70 | 393 nm | 25 |
| 10%(w/w) PVA | 100 | 149 nm | 35 |
| Large Nanoparticles (221 nm) | | | |
| 1%(w/w) PVA | 10 | 17 µm | 6 |
| 3%(w/w) PVA | 30 | 260 nm | 11 |
| 5%(w/w) PVA | 50 | 243 nm | 17 |
| 7%(w/w) PVA | 70 | 241 nm | 20 |
| 10%(w/w) PVA | 100 | 240 nm | 24 |

EXAMPLE 3

Protein Adsorption Efficiency for Nanoparticles and Microparticles

For the same particle mass, nanoparticles have a much larger surface area as compared to microparticles. In this case, the nanoparticles allow for more efficient protein loading per particle mass compared to the 1 µm microparticles. This allows for the delivery of the same amount of protein antigen with less PLG (and consequently less total surfactant).

A model antigen, bovine serum albumin (BSA), was added to the nanoparticle or microparticle suspension with the appropriate buffer and agitated on a lab rocker at 4° C. overnight. The nanoparticles were separated by centrifugation. The pellets were hydrolyzed overnight at 25° C. with 0.2N NaOH. The protein concentration in the supernatant and in the hydrolyzed pellet was determined by a BCA™ assay (from Pierce, Rockford, Ill., USA). As shown in FIG. 1, BSA showed increased loading efficiency on the nanoparticles, as compared to the microparticles, at two pH values, after 24 hours of adsorption. The increased loading efficiency allowed for up to 3.5% adsorption (wt. BSA/wt. PLG) on the nanoparticles, compared to a maximum loading of 1.5% (wt. BSC/wt. PLG) for the microparticles.

This enhanced adsorption was particularly noticeable at pH=7, where the microparticles were essentially resistant to adsorption, while the nanoparticles allowed significant adsorption to occur. Thus, it can be seen that the nanoparticles allowed for significant adsorption under otherwise unfavorable adsorption conditions. This can be useful for particle formulations in which the pH needs to be set at a particular value, for example, to enhance antigen stability, among other reasons.

Figure 2:
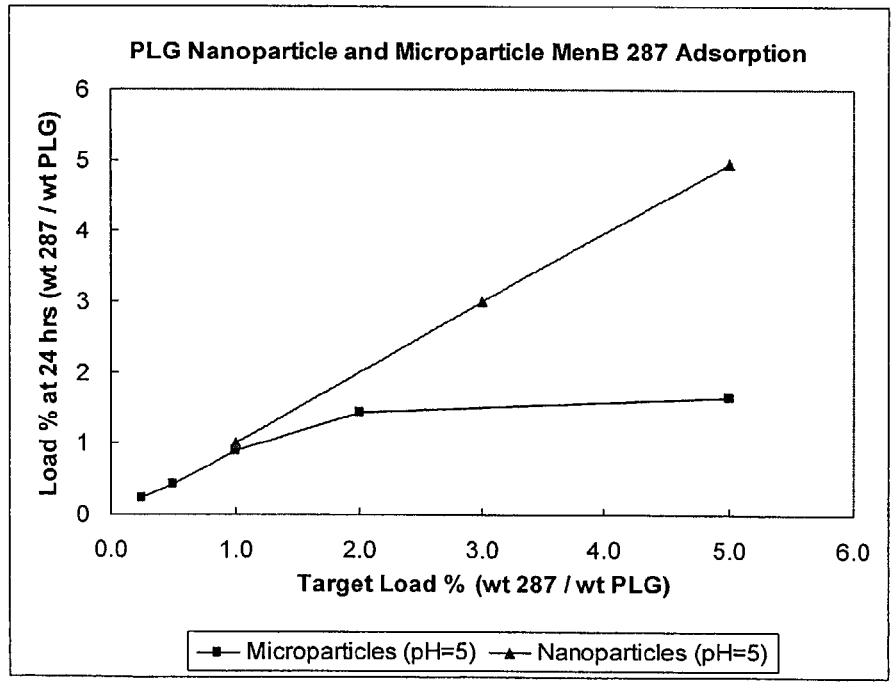
FIG. 2 depicts plots of MenB 287 loading on PLG microparticles and nanoparticles at pH=5.

An antigen from *Neisseria meningitidis* serotype B (i.e., Men B 287) was also adsorbed to nanoparticles and microparticles. In particular, the Men B 287 antigen was added to the nanoparticle or microparticle suspension in 10 mM citrate buffer at pH=5.0 and agitated on a lab rocker at 4° C. overnight. The particles were separated by centrifugation. The pellets were hydrolyzed overnight at 25° C. with 0.2N NaOH. The protein concentrations in the supernatant and in the hydrolyzed pellet were determined by a BCA™ assay (Pierce). As seen from FIG. 2, as with the BSA, the nanoparticles displayed enhanced adsorption of Men B 287 as compared to the microparticles.

Resuspension following antigen adsorption and lyophilization was also an important characteristic of the certain compositions of the invention. In this example, proteins, specifically, BSA, Ovalbumin, FluCC, Men B 287, Men B 287 or GBS1 were added to the nanoparticle suspension in Histidine buffer at pH 5 and agitated on a lab rocker at 4° C. overnight. Initial particle size was ~120 nm. Surfactant and cryoprotective agents were added in accordance with Table 3, and the mixture lyophilized. After lyophilization 5-10 mg of nanoparticles were resuspended in 1 ml of water and sized. The nanoparticles were separated by centrifugation. The amount remaining in the supernatant (not adsorbed) was determined by HPLC size exclusion chromatography, absorbance at 214 nm. As can be seen from Table 4, nanoparticles with adsorbed proteins substantially retained their small size and have high protein adsorption efficiency for target loads of 1% (w/w) and 5% (w/w).

TABLE 4

| Protein Adsorbed | Excipient | Final size | % Adsorbed |
|---|---|---|---|
| 1% (w/w) OVA | 0.5% (w/w) DSS/ 5% trehalose + 2.5% mannitol (w/v) | 173 nm | 98 |
| 1% (w/w) BSA | 0.5% (w/w) DSS/ 5% trehalose + 2.5% mannitol (w/v) | 143 nm | 100 |
| 5% (w/w) BSA | 0.5% (w/w) DSS/ 5% trehalose + 2.5% mannitol (w/v) | 134 nm | 71 |
| 1% (w/w) BSA | 10% PVA (w/w)/ 4% sucrose + 3% mannitol (w/v) | 216 nm | 94 |
| 1% (w/w) FluCC | 0.5% (w/w) DSS/ 5% trehalose + 2.5% mannitol (w/v) | 242 nm | 100 |
| 1% (w/w) Men B 287 | 0.5% (w/w) DSS/ 5% trehalose + 2.5% mannitol (w/v) | 4850 µm | 85 |
| 5% (w/w) Men B 287 | 0.5% (w/w) DSS/ 5% trehalose + 2.5% mannitol (w/v) | 167 nm | 95 |
| 1% (w/w) Men B 287 | 10% PVA (w/w)/ 4% sucrose + 3% mannitol (w/v) | 192 nm | 77 |
| 5% (w/w) Men B 287 | 10% PVA (w/w)/ 4% sucrose + 3% mannitol (w/v) | 169 nm | 80 |

TABLE 4-continued

| Protein Adsorbed | Excipient | Final size | % Adsorbed |
|---|---|---|---|
| 1% (w/w) GBS1 | 0.5% (w/w) DSS/ 5% trehalose + 2.5% mannitol (w/v) | 23 μm | 99 |
| 5% (w/w) GBS1 | 0.5% (w/w) DSS/ 5% trehalose + 2.5% mannitol (w/v) | 201 nm | 93 |

The amount of protein associated with the nanoparticles post-lyophilization (% protein adsorbed) was high, ranging from 71% to 100%, in examining the effect of protein concentration, and it was found that higher protein loading levels (wt. protein/wt. PLG) were easier to resuspend. The PVA excipient mixture resuspended nanoparticles with Men B 287 antigen at the lower loading level whereas the DSS excipient mixture did not. Similarly, for GBS1 antigen, the DSS excipient mixture, the higher 5% protein loaded formulation resuspended, while the lower 1% load did not. BSA resuspended at both lower and higher loadings. The resuspension with protein adsorption thus appears to be protein dependent, and can be evaluated for each protein antigen. The availability of multiple different excipient combinations offers flexibility in the event one combination is not sufficient for a particular protein.

EXAMPLE 4

In Vivo Studies

A microparticle suspension was prepared as previously described in Example 1. For groups 3-6 and 9-12 in Tables 5 and 6 below, Men B 287 was added to the microparticle or nanoparticle suspension at a target load of 1% or 5% (wt 287/wt PLG) in 10 mM histidine buffer at pH=5.5 and agitated on a lab rocker at 4° C. overnight. Surfactant and cryoprotective agents were added and the mixture lyophilized.

For Groups 3 and 9, Men B 287 was adsorbed at 1% (wt 287/wt PLG) load with only the 0.05% DSS (wt/wt PLG) from the initial particle preparation as surfactant and 4% sucrose (wt/volume) and 3% mannitol (wt/volume) as a cryoprotectant. For Groups 4 and 10, Men B 287 was adsorbed at 1% (wt 287/wt PLG) load with the addition of 10% PVA (wt PVA/wt PLG) plus 4% sucrose (wt/volume) and 3% mannitol (wt/volume). For Groups 5 and 11, Men B 287 was adsorbed at 5% (wt 287/wt PLG) load with the addition of 0.5% DSS (wt DSS/wt PLG) plus 5% trehalose (wt/volume) and 2.5% mannitol (wt/volume). For Groups 6 and 12, Men B 287 was adsorbed at 5% (wt 287/wt PLG) load with the addition of 10% PVA (wt PVA/wt PLG) plus 4% sucrose (wt/volume) and 3% mannitol (wt/volume). After lyophilization, microparticles corresponding to a total dose of 1 μg and 10 μg Men B 287, respectively, were reconstituted with 1.2 ml Water for Injection. Reconstituted samples were sized with a Zetasizer 3000HSA for the nanoparticles and a Horiba LA 930 for the microparticles. The results are presented in Table 5.

For Groups 2 and 8, an MF59 emulsion (Chiron Vaccines) was mixed with 2×PBS and either 1 μg or 10 μg of Men B 287 immediately prior to immunization.

For Groups 1 and 7 Men B 287 was added to aluminum hydroxide (Chiron Vaccines) in 10 mM histidine buffer at pH=5.5 plus 9 mg/mL NaCl and agitated on a lab rocker at 4° C. overnight with an alum concentration of 2 mg/mL.

For all groups, samples were injected IM into groups of 10 female CD-1 mice on day(s) 0, 21 and 35. For groups 3-6 and 9-12, lyophilized microparticles or nanoparticles were reconstituted with Water for Injection. Groups 1, 2, 7 and 8 were used as described. At day 49, serum ELISA titers (IgG, IgG1, IgG2a) are analyzed as described in Singh, M., et al. (2004) (J. Pharm. Sci. 93(2): 273-282), and serum bactericidal activity (SBA) was analyzed as described in Pizza, M., et al. (2000) (Science 287(5459):1816-1820). 2996 was the strain of MenB used for SBA analysis. The results are presented in Table 6 below.

The in vivo study finds that nanoparticles and microparticles are comparable for both doses based on serum titers and SBA. The MF59 at the high dose is significantly different for IgG than all other groups ($p<0.05$ with two tail student t-test assuming unequal variance). Groups 1 and 4 IgG titers are significantly different from group 6 ($p<0.05$ with two tail student t-test assuming unequal variance), however this result is not true for the SBA, which is the more important endpoint of the study.

TABLE 5

| Group | Formulation | Size* (nm) | pH |
|---|---|---|---|
| 1 | Alum/287, 1 ug | — | 5.8 |
| 2 | MF59/287, 1 ug | — | — |
| 3 | PLG/MP/287, 1 ug | 805 | 5.0 |
| 4 | PLG/NP/287/1% load/PVA, 1 ug | 158 | 5.0 |
| 5 | PLG/NP/287/5% load/DSS, 1 ug | 149 | 5.0 |
| 6 | PLG/NP/287/5% load/PVA, 1 ug | 149 | 5.0 |
| 7 | Alum/287, 10 ug | — | 5.5 |
| 8 | MF59/287, 10 ug | — | — |
| 9 | PLG/MP/287, 10 ug | 790 | 5.8 |
| 10 | PLG/NP/287/1% load/PVA, 10 ug | 123 | 5.3 |
| 11 | PLG/NP/287/5% load/DSS, 10 ug | 140 | 5.5 |
| 12 | PLG/NP/287/5% load/PVA, 10 ug | 160 | 5.3 |

*size is post lyophlization

TABLE 6

| | | | | | |
|---|---|---|---|---|---|
| 1 | Alum/287, 1 ug | 130 | 2,035 | 51 | 64 |
| 2 | MF59/287, 1 ug | 1,889 | 2,829 | 304 | 128 |
| 3 | PLG/MP/287, 1 ug | 1,023 | 1,861 | 36 | 64 |
| 4 | PLG/NP/287/1% load/PVA, 1 ug | 326 | 1,008 | 168 | 32 |
| 5 | PLG/NP/287/5% load/DSS, 1 ug | 758 | 2,663 | 94 | 64 |
| 6 | PLG/NP/287/5% load/PVA, 1 ug | 2,466 | 7,824 | 312 | 64 |
| 7 | Alum/287, 10 ug | 2,252 | 15,496 | 142 | 128 |
| 8 | MF59/287, 10 ug | 29,743 | 18,253 | 6,569 | 2048 |
| 9 | PLG/MP/287, 10 ug | 8,340 | 19,258 | 628 | 256 |
| 10 | PLG/NP/287/1% load/PVA, 10 ug | 7,567 | 20,575 | 565 | 128 |
| 11 | PLG/NP/287/5% load/DSS, 10 ug | 1,986 | 9,197 | 160 | 64 |
| 12 | PLG/NP/287/5% load/PVA, 10 ug | 4,348 | 15,746 | 373 | 128 |

Although preferred embodiments of the subject invention have been described in some detail, it is understood that obvious variations can be made without departing from the spirit and the scope of the invention.

The invention claimed is:

1. A sterile filtered lyophilized nanoparticle composition comprising (a) a biodegradable polymer, (b) a surfactant, (c) a cryoprotective agent, and (d) an antigen, wherein the composition does not comprise a polyoxyethylene block co-polymer and wherein the cryoprotective agent is present in an effective amount to allow for particle resuspension without aggregation.

2. The composition of claim 1, wherein upon mixing lyophilized nanoparticle compositions of the present invention with distilled water in a concentration of 0.005 g/ml, an immunogenic nanoparticle suspension is spontaneously formed in which the Z average particle size of said suspended nanoparticles is less than 250 nm.

3. The composition of claim 1 or claim 2, wherein the Z average particle size of said suspended nanoparticles is less than 200 nm.

4. The composition claim 1, wherein the Z average particle size of said suspended nanoparticles is less than 150 nm.

5. The composition of claim 1, wherein said surfactant is poly(vinyl alcohol).

6. The composition of claim 1, wherein said surfactant is dioctyl sodium sulfosuccinate.

7. The composition of claim 1, wherein the antigen comprises a polypeptide containing antigen.

8. The composition of claim 1, wherein the antigen comprises a subunit antigen.

9. The composition of claim 1, wherein the antigen comprises a polysaccharide-containing antigen.

10. The composition of claim 1, wherein the antigen comprises a conjugate antigen.

11. The composition of claim 1, wherein the antigen comprises a polynucleotide-containing antigen.

12. The composition of claim 11, wherein the polynucleotide-containing antigen comprises a vector construct that encodes a polypeptide-containing antigen.

13. The composition of claim 1, wherein the antigen comprises a tumor-cell-derived antigen.

14. The composition of claim 1, wherein the antigen comprises a pathogenic-organism-derived antigen.

15. The composition of claim 14, wherein the antigen is derived from a pathogenic organism selected from a virus, a bacterium, a fungus and a parasite.

16. The composition of claim 14, wherein the antigen is derived from a pathogenic organism selected from hepatitis virus, varicella, poliovirus, measles, mumps, rubella, influenza virus, *Neisseria meningitidis*, pertussis, *Haemophilus influenzae* type b, human immunodeficiency virus (HIV), and *Streptococcus pneumoniae*.

17. The composition of claim 1, wherein the antigen is adsorbed on the surfaces of the nanoparticles.

18. The composition of claim 1, wherein the antigen is entrapped within the nanoparticles.

19. The composition of claim 1, further comprising an immunological adjuvant.

20. The composition of claim 19, wherein the immunological adjuvant is adsorbed to the surface of the suspended nanoparticles.

21. The composition of claim 19, wherein the immunological adjuvant is entrapped within the suspended nanoparticles.

22. The composition of claim 19, wherein the immunological adjuvant is selected from CpG oligonucleotides, double-stranded RNA, *E. coli* heat-labile toxins, alum, liposaccharide phosphate compounds, and liposaccharide phosphate mimetics.

23. The composition of claim 1, wherein said immunogenic composition is sterilized by filtration prior to lyophilization.

24. A method of stimulating an immune response in a vertebrate host, comprising: combining the composition of claim 1 with an aqueous fluid to form a suspension; and administering the suspension to the host in an amount effective to induce an immune response.

25. The method of claim 24, wherein said suspension is injected into said vertebrate host.

26. The method of claim 24, wherein said vertebrate host is a human.

27. The method of claim 24, wherein the immune response comprises a cellular immune response.

28. The method of claim 24, wherein the immune response comprises a Th1 immune response.

29. The method of claim 24, wherein the immune response comprises a CTL immune response.

30. The method of claim 24, wherein the immune response is raised against a viral, bacterial, fungal or parasitic infection.

31. A method of immunizing a vertebrate host against a tumor or a pathogenic organism, comprising: combining the composition of claim 1 with an aqueous fluid to form a suspension; and administering the suspension to the host in an amount effective to induce a' protective response.

32. A method of treating a tumor or a pathogenic organism infection in a vertebrate host, comprising: combining the composition of claim 1 with an aqueous fluid to form a suspension; and administering the suspension to the host in an amount effective to induce a treatment response.

33. A method of producing the composition of claim 1, comprising: (a) combining (i) a first liquid that comprises said biodegradable polymer dissolved in an organic solvent with (ii) a second liquid that comprises water, whereupon a suspension of nanoparticles comprising said biodegradable polymer is formed, (b) adsorbing said antigen to said nanoparticles to form an antigen-adsorbed nanoparticle suspension, and (c) lyophilizing said antigen-adsorbed nanoparticle suspension.

34. The method of claim 33, wherein said cryoprotective agent is added immediately prior to lyophilization.

35. The method of claim 33, further comprising sterile filtering said nanoparticle suspension and said antigen prior to adsorbing said antigen to said nanoparticles.

36. The method of claim 33, further comprising sterile filtering said antigen-adsorbed nanoparticle suspension prior to lyophilization.

37. A kit comprising a first container comprising the lyophilized nanoparticle composition of claim 1.

38. The kit of claim 37, further comprising a second container comprising a sterile liquid medium useful to resuspend the lyophilized nanoparticle composition in the first container.

39. The kit of claim 37, further comprising a syringe.

40. The composition of claim 1, wherein the antigen is selected from a pathogenic-organism-derived antigen and a tumor-cell-derived antigen.

41. The composition of claim 1, wherein the cryoprotective agent comprises a saccharide.

42. The composition of claim 41, wherein said saccharide is trehalose.

43. The composition of claim 41, wherein said saccharide is sucrose.

44. The composition of claim 1, wherein the cryoprotective agent comprises an alditol.

45. The composition of claim 44, wherein said alditol is mannitol and wherein said surfactant is selected from an anionic surfactant and a non-ionic surfactant.

46. The composition of claim 44, wherein said alditol is mannitol and wherein said surfactant is a non-ionic surfactant.

47. A sterile filtered lyophilized nanoparticle composition comprising (a) a biodegradable polymer selected from a poly(α-hydroxy acid), a polyhydroxy butyric acid, a polycaprolactone, a polyorthoester, a polyanhydride, a polycyanoacrylate and combinations thereof, (b) a surfactant, (c) a cryoprotective agent, and (d) an antigen, wherein the cryoprotective agent is present in an effective amount to allow for particle resuspension without aggregation.

48. The composition of claim 47, wherein the composition comprises the poly(α-hydroxy acid) and the poly(α-hydroxy acid) is selected from poly(lactide), poly(glycolide), poly(lactide-co-glycolide) and combinations thereof.

49. The composition of claim 48, wherein the composition comprises the poly(lactide-co-glycolide) and the poly(lactide-co-glycolide) has a lactide:glycolide molar ratio ranging from 40:60 to 60:40.

* * * * *